US010890588B2

(12) United States Patent
Fante et al.

(10) Patent No.: US 10,890,588 B2
(45) Date of Patent: Jan. 12, 2021

(54) COMPOSITIONS AND METHODS FOR DETECTING CANCER CELLS IN A TISSUE SAMPLE

(71) Applicant: ISI Life Sciences, Inc., Newport Beach, CA (US)

(72) Inventors: John Fante, Newport Beach, CA (US); Theodore Hessler, III, Newport Beach, CA (US); Robert M. Moriarty, Michiana Shores, MI (US); Richard Pariza, Chicago, IL (US); Gerald F. Swiss, San Diego, CA (US); David White, Newport Beach, CA (US); Craig Keshishian, Newport Beach, CA (US)

(73) Assignee: ISI Life Sciences, Inc., Newport Beach, CA (US)

( * ) Notice: Subject to any disclaimer, the term of this patent is extended or adjusted under 35 U.S.C. 154(b) by 298 days.

(21) Appl. No.: 15/693,218

(22) Filed: Aug. 31, 2017

(65) Prior Publication Data

US 2018/0209986 A1    Jul. 26, 2018

Related U.S. Application Data

(63) Continuation of application No. PCT/US2017/048083, filed on Aug. 22, 2017, and a continuation-in-part of application No. PCT/US2017/045178, filed on Aug. 2, 2017.

(60) Provisional application No. 62/378,128, filed on Aug. 22, 2016, provisional application No. 62/393,523, filed on Sep. 12, 2016, provisional application No. 62/370,130, filed on Aug. 2, 2016.

(51) Int. Cl.
*G01N 33/48* (2006.01)
*G01N 33/50* (2006.01)
*G01N 33/58* (2006.01)
*A61K 49/00* (2006.01)
*C07D 493/10* (2006.01)
*C09K 11/07* (2006.01)
*G01N 33/574* (2006.01)
*C09B 11/22* (2006.01)
*C07D 407/04* (2006.01)

(52) U.S. Cl.
CPC ......... *G01N 33/582* (2013.01); *A61K 49/006* (2013.01); *A61K 49/0041* (2013.01); *A61K 49/0043* (2013.01); *A61K 49/0058* (2013.01); *A61K 49/0071* (2013.01); *C07D 407/04* (2013.01); *C07D 493/10* (2013.01); *C09B 11/22* (2013.01); *C09K 11/07* (2013.01); *G01N 33/574* (2013.01); *G01N 33/57484* (2013.01); *G01N 2800/7028* (2013.01)

(58) Field of Classification Search
None
See application file for complete search history.

(56) References Cited

U.S. PATENT DOCUMENTS

| | | |
|---|---|---|
| 3,806,592 A | 4/1974 | Imondi |
| 6,455,268 B1 | 9/2002 | Jarnigan et al. |
| 6,872,871 B2 | 3/2005 | Brisson et al. |
| 6,875,850 B2 | 4/2005 | Heindl et al. |
| 7,758,891 B2 | 7/2010 | Desai et al. |
| 7,820,788 B2 | 10/2010 | Desai et al. |
| 7,923,536 B2 | 4/2011 | Desai et al. |
| 7,955,832 B2 | 6/2011 | Michnick et al. |
| 8,034,375 B2 | 10/2011 | Desai et al. |
| 8,043,602 B2 | 10/2011 | Jallad et al. |
| 8,043,603 B2 | 10/2011 | Kennedy et al. |
| 8,044,200 B2 | 10/2011 | Xu et al. |
| 8,138,229 B2 | 3/2012 | Desai et al. |
| 8,192,944 B2 | 6/2012 | Michnick et al. |
| 8,268,348 B2 | 9/2012 | Desai et al. |
| 8,314,156 B2 | 11/2012 | Desai et al. |
| 8,420,396 B2 | 4/2013 | Uhlmann et al. |
| 8,795,633 B2 | 8/2014 | Low |
| 8,853,260 B2 | 10/2014 | Desai et al. |
| 8,858,914 B2 | 10/2014 | Kennedy et al. |
| 8,865,128 B2 | 10/2014 | Jallad et al. |
| 9,101,543 B2 | 8/2015 | Desai et al. |

(Continued)

FOREIGN PATENT DOCUMENTS

| | | | | |
|---|---|---|---|---|
| WO | 9931267 A1 | 6/1999 | | |
| WO | WO-2005045734 A1 * | 5/2005 | ............... | G06T 5/30 |

(Continued)

OTHER PUBLICATIONS

US 9,926,334 B1, 03/2018, Swiss (withdrawn)
Abbasi, et al., "Cationic Albumin Nanoparticles for Enhanced Drug Delivery to Treat Breast Cancer: Preparation and In Vitro Assessment," Journal of Drug Delivery, pp. 1-8, 2012.
Feng et al., "Distinguishing folate-receptor-positive cells from folate-receptor-negative cells using a fluorescence off-on nanoprobe", Anal. Chem., 2013, 85(13):6530-6535.
Liu, Jidong, "Design and synthesis of folic acid conjugates as cancer diagnostic and treatment agents", The University of Toledo, ProQuest Dissertations Publishing, 2007. (248 pages).
Lu et al., "Preclinical pharmacokinetics, tissue distribution, and antitumor activity of a folate-hapten conjugate-targeted immunotherapy in hapten-immunized mice", Mol. Cancer Ther., 2006, 5(12):3258-3267.

(Continued)

*Primary Examiner* — Russell S Negin
(74) *Attorney, Agent, or Firm* — Procopio, Cory, Hargreaves & Savitch LLP

(57) ABSTRACT

This invention is directed to methods for the facile and accurate identification of cancer cells in a tissue sample, such as a surgical field. In particular, the compositions and methods employ conjugates comprising pro-fluorescent fluorescein based moieties bound to folic or pteroic acid targeting moiety optionally through a linker. The pro-fluorescent fluorescein based moieties are non-fluorescent but capable of being rendered fluorescent by intracellular processes. The conjugates are employed to detect cancer cells that overexpress folic acid receptors thereby providing for differential accumulation of these conjugates in these cells.

3 Claims, 1 Drawing Sheet

(56) References Cited

U.S. PATENT DOCUMENTS

| | | |
|---|---|---|
| 9,279,813 B2 | 3/2016 | Low et al. |
| 9,486,535 B2 | 11/2016 | Wagner et al. |
| 9,549,992 B2 | 1/2017 | Leamon et al. |
| 9,731,035 B2 | 8/2017 | Low |
| 10,239,891 B2 | 3/2019 | Swiss |
| 10,363,250 B2 | 7/2019 | Leamon |
| 10,539,567 B2 | 1/2020 | Swiss et al. |
| 2003/0162234 A1 | 8/2003 | Jallad |
| 2004/0136910 A1 | 7/2004 | Jallad et al. |
| 2005/0202518 A1 | 9/2005 | Vedrine et al. |
| 2006/0128033 A1 | 6/2006 | Suich et al. |
| 2007/0027075 A1 | 2/2007 | Smithrud |
| 2008/0014147 A1 | 1/2008 | Nagano et al. |
| 2009/0012009 A1 | 1/2009 | Low et al. |
| 2010/0027267 A1 | 10/2010 | Leamon |
| 2010/0272675 A1 | 10/2010 | Leamon et al. |
| 2010/0322919 A1 | 12/2010 | Chalal et al. |
| 2011/0129419 A1 | 6/2011 | Storey et al. |
| 2011/0177619 A1 | 7/2011 | Metters et al. |
| 2013/0266964 A1 | 10/2013 | Low |
| 2013/0344002 A1 | 12/2013 | Jallad et al. |
| 2014/0005141 A1 | 1/2014 | Amit et al. |
| 2014/0171635 A1 | 6/2014 | Schwartz et al. |
| 2014/0227297 A1 | 8/2014 | Goonewardena et al. |
| 2014/0248218 A1 | 9/2014 | Daniel et al. |
| 2014/0271476 A1 | 9/2014 | Kularatne et al. |
| 2015/0057433 A1 | 2/2015 | Deming et al. |
| 2015/0320079 A1 | 11/2015 | Low |
| 2016/0083424 A1 | 3/2016 | Sioud et al. |
| 2017/0128595 A1 | 5/2017 | Swiss et al. |
| 2017/0234878 A1 | 8/2017 | Swiss |
| 2018/0036312 A1 | 2/2018 | Swiss et al. |
| 2018/0209986 A1 | 7/2018 | Fante |
| 2018/0327424 A1 | 11/2018 | Swiss |
| 2018/0328933 A1 | 11/2018 | Swiss |
| 2019/0107543 A1 | 4/2019 | Moriarty |
| 2019/0227066 A1 | 7/2019 | Fante |
| 2020/0150127 A1 | 5/2020 | Swiss |

FOREIGN PATENT DOCUMENTS

| | | | |
|---|---|---|---|
| WO | 2010036821 A1 | 4/2010 | |
| WO | 2015024576 A1 | 2/2015 | |
| WO | 2015073678 A1 | 5/2015 | |
| WO | WO-2016/123244 A1 | 8/2016 | |

OTHER PUBLICATIONS

Nottelet et al., "Redox and thiol-ene cross-linking of mercapto poly (∈-caprolactone) for the preparation of reversible degradable elastomeric materials", Polym. Chem., 2012, 3, 2956-2963.

Ogawa et al., "Fluorophore-Quencher Based Activatable Targeted Optical Probes for Detecting in Vivo Cancer Metastases", Molecular Pharaceutics, vol. 6, pp. 386-395, 21 Jan. 21, 2009.

Oheim et al., "Quantitative Colocalisation Imaging: Concepts, Measurements, and Pitfalls", In: Shorte S.L., Frischknecht F. (eds) Imaging Cellular and Molecular Biological Functions. Principles and Practice. Springer, 2007, 117-155.

PCT International Search Report and Written Opinion for Application No. PCT/US2017/013531 dated Jun. 9, 2017. (22 pages).

PCT International Search Report and Written Opinion for Application No. PCT/US2017/48083, dated Oct. 31, 2017. (26 pages).

Pubchem CID 101839416, Created Dec. 18, 2015.

Pubchem CID 102433897, Created Dec. 26, 2015.

Pubchem CID 81743, Created Aug. 8, 2005.

Roelants et al., "Use of Fluorescein Isolhicyanate-Human Serum . . . ," BJU International, Dec. 13, 2010, vol. 108, pp. 455-459.

Urano et al., "Evolution of Fluorescein as Platform for Finely Tunable Fluorescence Probes," Journal of the American Chemical Society, vol. 127, pp. 4888-4894, Mar. 10, 2015.

Van Dam et al., "Intraoperative tumor-specific fluorescence imaging in ovarian cancer by folate receptor-α targeting: first in-human results", Nature Medicine, 2011, 17, 1315-1319.

Xia et al., "Reliable and global measurement of fluorescence resonance energy transfer using fluorescence microscopes", Biophysical Journal, 2001, 81(4):2395-2402.

Kratz, Felix; "Albumin as a drug carrier: Design of prodrugs, drug conjugates and nanoparticles" Journal of Controlled Release, 132, 171-183, 2008.

International Search Report and Written Opinion for related PCT application No. PCT/US2017/043141, dated Nov. 27, 2017, 12 pages.

International Preliminary Report on Patentability for International Application No. PCT/US2017/043141, dated Feb. 5, 2019, 9 pages.

International Preliminary Report on Patentability for International Patent Application No. PCT/US2017/048083, dated Feb. 26, 2019, 14 pages.

Wang, M; Thanou, M; "Targeting nanoparticles to cancer," Pharmacological Research, 62, 90-99, 2010.

Rotman et al. "Membrane Properties of Living Mammalian Cells as Studied by Enzymatic Hydrolysis of Fluorogenic Esters," Biochemistry, 1966, vol. 55, pp. 134-141.

International Search Report for International Application No. PCT/US2017/045178, dated Nov. 13, 2017, 2 pages.

Written Opinion for International Application No. PCT/US2017/045178, dated Nov. 13, 2017, 5 pages.

International Preliminary Report on Patentability for International Application No. PCT/US20171045178, dated Feb. 5, 2019, 6 pages.

Robertson et al., "Fluorescein derivatives in intravital fluorescence imaging," Cell 2013, vol. 2, pp. 591-606, 2013.

Cheung, et al., Targeting folate receptor alpha for cancer treatment, Oncotarget, 2016, pp. 52553-52574, vol. 7, No. 32.

T.P. McAlinden et al., "Synthesis and Biological Evaluation of a Fluorescent Analogue of Folic Acid," Biochemistry. 30:5674-5681 (1991) 8 pages.

S.S. Dharap et al., "Tumor-Specific Targeting of an Anticancer Drug Delivery System by LHRH Peptide." PNAS. 102(36):12962-12967 (2005) 6 pages.

N.M. Green, "[73] Purification of avidin." Methods in Enzymology, vol. 18 (Academic Press, 1970) 414-417 (Year: 1970) 4 pages.

Kennedy et al., Evaluation of Folate Conjugate Uptake and Transport by the Choroid Plexus of Mice, (2003) Pharm. Res. 20:714-719, 7 pages.

* cited by examiner

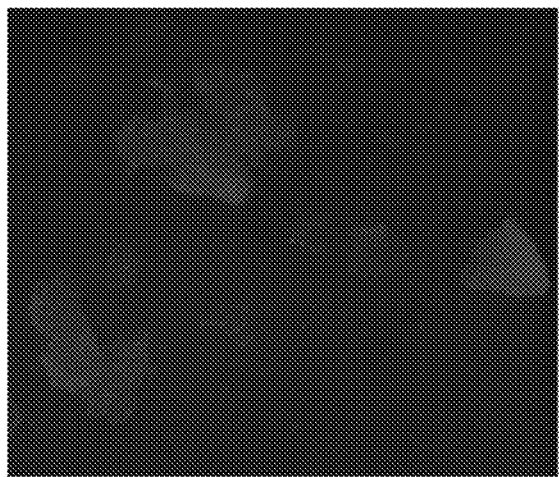
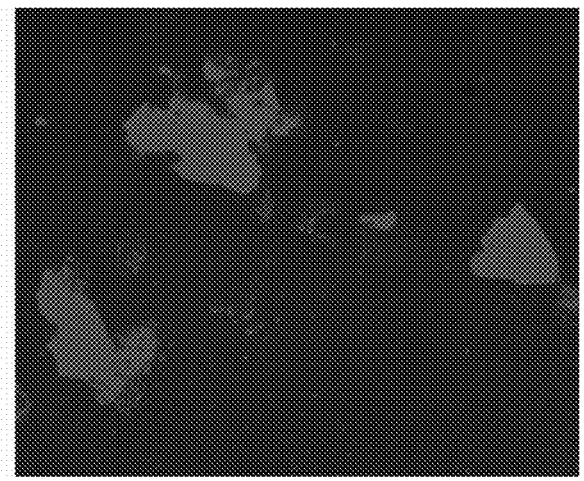
FIGURE 1          FIGURE 2
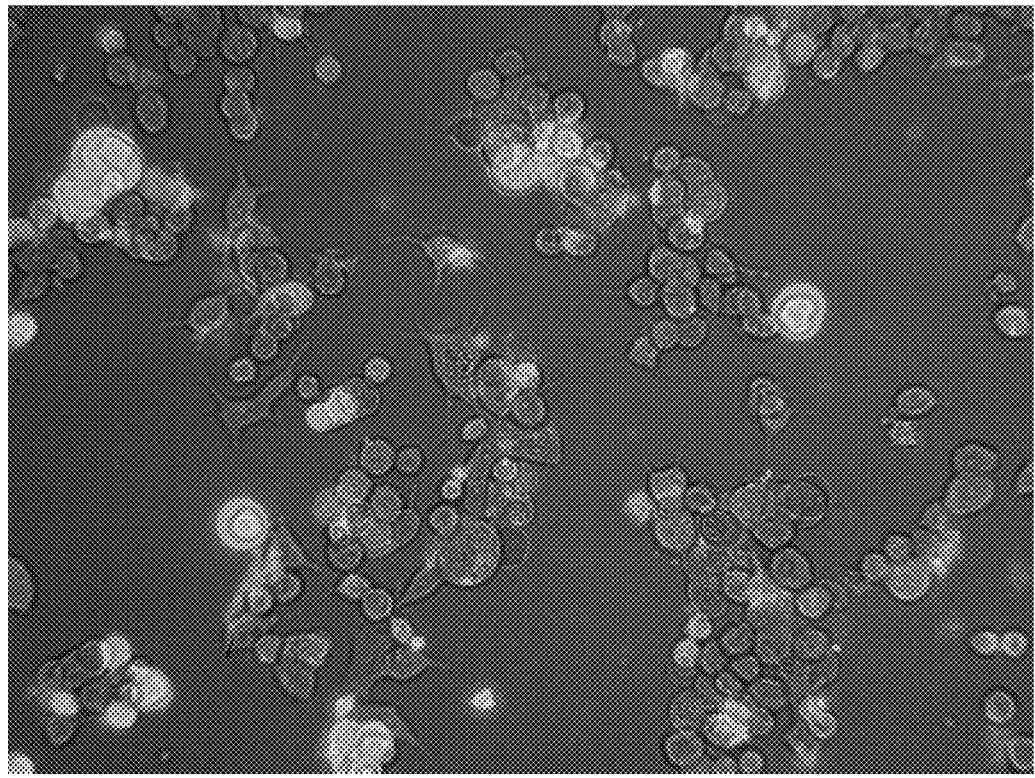
FIGURE 3

COMPOSITIONS AND METHODS FOR DETECTING CANCER CELLS IN A TISSUE SAMPLE

CROSS-REFERENCE TO RELATED APPLICATIONS

This application is a continuation of International Application No. PCT/US17/48083, filed Aug. 22, 2017, which claims priority to U.S. Provisional Application No. 62/378, 128, filed Aug. 22, 2016; and U.S. Provisional Application No. 62/393,523, filed Sep. 12, 2016, the contents of each of which is incorporated herein in its entirety by reference.

This application is a continuation-in-part application of International Application No. PCT/US17/45178, filed Aug. 2, 2017, which claims priority to U.S. Provisional Application No. 62/370,130, filed Aug. 2, 2016; U.S. Provisional Application No. 62/378,128, filed Aug. 22, 2016; and U.S. Provisional Application No. 62/393,523, filed Sep. 12, 2016; the contents of each of which is incorporated herein in its entirety by reference.

BACKGROUND OF THE INVENTION

Field of the Invention

This invention is directed to methods for the facile and accurate identification of cancer cells in a tissue sample. In particular, the methods employ a targeting agent that binds to and is absorbed by cancer cells that overexpress folic acid receptors. Advantageously, the targeting agent is conjugated to a pro-fluorescent fluorescein based compound that does not generate fluorescence until absorbed by such cancer cells whereupon intracellular processes convert the pro-fluorescent fluorescein moiety to a fluorescent moiety. The use of such a pro-fluorescent fluorescein moieties allow for computational removal of background fluorescence generated by a tissue sample including a number of factors such as aromatic amino acids in the tissue sample, bodily fluids that exhibit fluorescence, and the like. Accordingly, the methods described herein will provide a level of specificity for determining the presence of cancer cells in a surgical field or a tissue sample that are otherwise not obtainable by current technologies including evaluation of sub-visual fluorescence.

State of the Art

It is commonplace to conjugate a fluorescent tag to targeting agent so as to identify where the conjugate migrates in the body. When so used, detection of minute fluorescence levels is not as critical as locating the intense fluorescent signal generated. Simply put, the intense fluorescent signal allows the clinician to follow the conjugate to its primary target point dictated by the targeting agent on the conjugate.

In the treatment of cancer, evaluation of the surgical field after tumor resection to assess the presence of remnant cancer cells by fluorescent markers on conjugates used to bind to such cells is difficult. This is because the fluorescence generated by populations of just a few cancer cells is generally undetectable. Specifically, the surgical field contains numerous fluorescent-producing entities ranging from aromatic amino acids to other physiological components. This and other factors such as instrumentation limitations prevent the surgeon from assessing other than gross differences in fluorescence as a means to detect putative cancer cells. This, in turn, results in unacceptable levels of remnant cancer cells remaining in the patient after tumor resection thereby increasing the risk of relapses.

Accordingly, there is a need to provide for highly specific methods for detecting cancer cells that are able to distinguish between background fluorescence and fluorescence generated by remnant cancer cells.

SUMMARY OF THE INVENTION

This invention provides for methods to account for background fluorescence and then to differentiate such background fluorescence from the overall fluorescence to assess that fluorescence solely attributable to fluorescent fluorescein based moieties in remnant cancer cells. This approach allows for accurate assessment of cancer cells even at minute levels that previously would not have been possible.

Specifically, this invention employs conjugates comprising pro-fluorescent fluorescein based moieties bound to folic or pteroic acid targeting moiety optionally through a linker. The pro-fluorescent fluorescein based moieties are non-fluorescent but capable of being rendered fluorescent by intracellular processes. The conjugates are employed to detect cancer cells that overexpress folic acid receptors thereby providing for differential accumulation of these conjugates in these cells.

Background fluorescence of a cellular mass is evaluated prior to application of the conjugate composition to the mass to provide a fluorescent high-resolution digital photographic image, hereinafter referred to as the "before image". Subsequent application of conjugate composition to the cellular mass is followed by incubation to permit conjugate absorption into targeted cancer cells coupled with conversion of pro-fluorescent moieties to fluorescent moieties. Optionally, the cellular mass is washed to remove excess unabsorbed conjugated composition. An after fluorescent image of the tissue sample is conducted. The second and subsequent images are hereinafter referred to as "after images". The image differences between the before and after images can then be highlighted and saved as a third image, the "difference image", that identifies the fluorescence arising from the now fluorescent conjugates within targeted cancer cells.

In one embodiment, markers on the surgical field are provided to allow the before fluorescent image to be accurately aligned with the after fluorescent image so as to allow accurate differentiation of the before image versus the after image. Such differentiation is utilized to generate a third image, which highlights the fluorescence produced by the targeted cancer cells. This allows for differentiation of the background fluorescence of the before fluorescent image from the fluorescence of the after fluorescence images so as to provide for a true reading of the fluorescence due solely to the fluorescein based moieties of the conjugates.

In one embodiment, there provided is a method for assessing the presence of cancer cells in a tissue sample suspected of containing cancer cells that overexpress folate receptors which method comprises:

a) identifying that portion of fluorescence associated with background fluorescence;

b) measuring total fluorescence in a tissue sample wherein pro-fluorescent moieties are in their fluorescent mode due to absorption coupled with conversion of the pro-fluorescent moieties into fluorescent moieties in said cells;

c) adjusting the total fluorescence to account for background fluorescence to provide for differential fluorescence; and d) attributing differential fluorescence to cancer cells.

In another embodiment, there provided is a method for assessing the presence of cancer cells in a tissue sample suspected of containing cancer cells that overexpress folate receptors which method comprises:

a) evaluating the background fluorescence of said sample to provide for a before fluorescent image;

b) selecting one or more conjugates comprising a targeting moiety wherein said conjugate comprises a folic or pteroic acid targeting moiety covalently coupled to pro-fluorescent fluorescein based moiety optionally through a linker;

c) applying an effective amount of said conjugate to the tissue sample suspected of containing said cancer cells;

d) incubating said tissue sample and applied said conjugate for a sufficient period of time to allow the conjugate to bind to and be absorbed by said cancer cells coupled with conversion of the pro-fluorescent moiety to a moiety capable of fluorescing;

e) assessing fluorescence of the incubated tissue sample to provide for an after fluorescent image;

f) differentiating the before fluorescence image from the after fluorescence image to provide for a differential fluorescent map attributable to cancer cells generating fluorescence from the now fluorescent fluorescein based moieties; and g) attributing said differential fluorescent map to the presence of cancer cells.

In one embodiment, the before and after fluorescence images are stored electronically and generation of the differential fluorescence map is conducted using appropriate software. Such software preferably evaluates pixel-by-pixel and differentiates the before fluorescent image from the after fluorescent image to provide a map of differential fluorescence that is attributed to remnant cancer cells.

In another embodiment, the before and after images of the surgical field are generated with one or more markers placed thereon. This allows for the alignment of the before and after images in a manner that allows for accurate differentiation. Preferably, the number of markers ranges from 2 to 10. In some embodiments, the fluorescence is measured in multiple images at different angles so that the surgeon can evaluate an uneven surface as is typical for a tissue sample such as a surgical field.

BRIEF DESCRIPTION OF THE DRAWINGS

FIG. 1 is a picture of fluorescence generated by particles of an agar composition to which fluorescein has been injected.

FIG. 2 is a picture of the differential fluorescence obtained by comparing the picture of FIG. 1 against a picture of a non-fluorescent background on a pixel-by-pixel basis.

FIG. 3 is a picture of fluorescence generated by MCF7 cells after incubating with a fluorescent conjugate compound of the present disclosure.

DETAILED DESCRIPTION OF THE INVENTION

This invention provides for methods for the facile and accurate identification of cancer cells in a tissue sample.

Prior to discussing this invention in further detail, the following terms will be defined:

As used herein, the following definitions shall apply unless otherwise indicated. Further, if any term or symbol used herein is not defined as set forth below, it shall have its ordinary meaning in the art.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

"After image" or "after fluorescent image" refers to high-resolution digital camera pictures of fluorescent tissue samples containing or in contact with the present conjugates after the conjugates have been converted from a pro-fluorescent state to a fluorescent state. The images are stored in electronic form and can be displayed on typical computer or TV displays.

"Before image" or "before fluorescent image" refers to high-resolution digital camera pictures of tissue samples taken to determine background fluorescence. The images are saved in electronic form and can be displayed on typical computer or TV displays.

"Difference image" or "differential image" refers to high-resolution digital image generated by software that compares before and after images and identifies and highlights the pixels or cells that have different color values. The difference image thus highlights the portions of the tissue sample that are associated with cancer cells. Difference images are saved in electronic form and can be displayed on typical computer or TV displays.

"Alkyl" refers to monovalent saturated aliphatic hydrocarbyl groups having from 4 to 30 carbon atoms and preferably 5 to 20 carbon atoms that optionally may contain from 1 to 3 sites of vinyl (double bonds) or acetylene (triple bonds) unsaturation. This term includes, by way of example, linear and branched hydrocarbyl groups of from $C_4$ to $C_{30}$ such as n-pentyl, neopentyl, cyclopentyl, octyl, stearyl, olelyl, and the like. $C_x$ alkyl refers to an alkyl group having x number of carbon atoms.

"Alkylene" refers to a divalent alkyl group.

"Substituted alkyl" refers to an alkyl group having from 1 to 5, preferably 1 to 3, or more preferably 1 to 2 substituents selected from the group consisting of acyl, acyloxy, acylamino, alkoxy, substituted alkoxy, amino, substituted amino, azido, carboxyl, carboxyl ester, cyano, cycloalkyl, substituted cycloalkyl, halo, phenyl, substituted phenyl, heteroaryl, substituted heteroaryl, hydroxy, heterocyclic, substituted heterocyclic, heterocyclyloxy, substituted heterocyclyloxy, hydroxy, and nitro, wherein said substituents are defined herein. In one embodiment, a preferred substituted alkyl group is —$CH_2CH_2C(O)OCH_2CH_2OCH_3$.

"Substituted alkylene" refers to a divalent substituted alkyl group.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl).

"Acyl" refers to the groups alkyl-C(O)—, substituted alkyl-C(O)—, phenyl-C(O)—, substituted phenyl-C(O)—, heteroaryl-C(O)—, cycloalkyl-C(O)—, substituted cycloalkyl-C(O)—, heteroaryl-C(O)—, substituted heteroaryl-C(O)—, heterocyclic-C(O)—, and substituted heterocyclic-C(O)—, isocyanate, isothiocyanate.

"Acyloxy" refers to the group —O-acyl wherein acyl is defined herein.

"Acylamino" refers to the groups -acyl-amino and -acyl-substituted amino.

"Amino" refers to the group —NH$_2$.

"Substituted amino" refers to the group —NR$^1$R$^2$ where R$^1$ and R$^2$ are independently selected from the group consisting of hydrogen, alkyl, substituted alkyl, phenyl, substituted phenyl, heteroaryl, substituted heteroaryl, heterocyclic, substituted heterocyclic, and wherein R$^1$ and R$^2$ are optionally joined, together with the nitrogen bound thereto to form a heterocyclic or substituted heterocyclic group, provided that R$^1$ and R$^2$ are both not hydrogen.

"Phenyl" refers to a monovalent aromatic carbocyclic group having 6 carbon atoms having a single ring.

"Substituted phenyl" refers to phenyl groups which are substituted with 1 to 5, preferably 1 to 3, or more preferably 1 to 2 substituents selected from the group consisting of alkyl, substituted alkyl, alkoxy, substituted alkoxy, acyl, acylamino, acyloxy, amino, substituted amino, carboxyl, carboxyl ester, cyano, halo, hydroxy, heteroaryl, substituted heteroaryl, heterocyclic, substituted heterocyclic, and nitro.

"Carbonyl" refers to the divalent group —C(O)— which is equivalent to —C(=O)—.

"Carboxy" or "carboxyl" refers to —COOH or salts thereof.

"Carboxyl ester"/"carboxy ester" refers to the groups —C(O)O-alkyl, —C(O)O-substituted alkyl, —C(O)O-cycloalkyl, —C(O)O-substituted cycloalkyl, —C(O)O-cycloalkenyl, —C(O)O-substituted cycloalkenyl, —C(O)O-phenyl, —C(O)O-substituted phenyl, —C(O)O-heteroaryl, —C(O)O-substituted heteroaryl, —C(O)O-heterocyclic, and —C(O)O-substituted heterocyclic.

"Conjugate" refers to a covalently linked fluorescent or pro-fluorescent molecule to folic or pteroic acid optionally through a linker.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings wherein such additional rings can be phenyl substituted phenyl, cycloalkyl and the like provide that the point of attachment is through the cycloalkenyl ring. Such cycloalkenyl groups have at least one >C=C< ring unsaturation and preferably from 1 to 2 sites of >C=C< ring unsaturation and optionally have 1 to 2 carbon atoms replaced by an oxygen atom.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkoxy, substituted alkoxy, amino, substituted amino, acyl, acyloxy, acylamino, azido, isocyanate, isothiocyanate, phenyl, substituted phenyl, carboxy, carboxy ester, cyano, cycloalkyl, substituted cycloalkyl, cycloalkenyl, substituted cycloalkenyl, halo, hydroxy, heteroaryl, substituted heteroaryl, heterocyclic, substituted heterocyclic (including maleimide), and nitro. One example of a substituted cycloalkenyl group includes

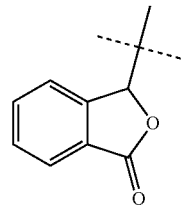

"Halo" or "halogen" refers to chloro, bromo and iodo.

"Hydroxy" or "hydroxyl" refers to the group —OH.

"Heteroaryl" refers to an aromatic heteroaryl group having from 1 to 10 carbon atoms and 1 to 4 heteroatoms selected from the group consisting of oxygen, sulfur, —SO—, —SO$_2$—, nitrogen, >NR$^3$ where R$^3$ is hydrogen or C$_1$-C$_6$ alkyl.

"Substituted heteroaryl" refers to heteroaryl groups substituted with 1 to 5, preferably 1 to 3, or more preferably 1 to 2 substituents selected from the group consisting of alkyl, substituted alkyl, alkoxy, substituted alkoxy, acyl, acylamino, acyloxy, amino, substituted amino, carboxyl, carboxyl ester, cyano, halo, hydroxy, heteroaryl, substituted heteroaryl, heterocyclic, substituted heterocyclic, and nitro.

"Heterocycle" or "heterocyclic" or "heterocycloalkyl" or "heterocyclyl" refers to a saturated group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems.

"Substituted heterocyclic" refers to heterocyclic groups substituted with 1 to 5 or preferably 1 to 3 substituents selected from the group consisting of oxo, thioxo, alkyl, substituted alkyl, alkoxy, substituted alkoxy, amino, substituted amino, acyl, acyloxy, acylamino, azido, phenyl, substituted phenyl, carboxy, carboxy ester, cyano, cycloalkyl, substituted cycloalkyl, cycloalkenyl, substituted cycloalkenyl, halo, hydroxy, heteroaryl, substituted heteroaryl, heterocyclic, substituted heterocyclic, and nitro.

"Marker" refers to a component that identifies a particular coordinate on a fluorescent image. The component can be any material that self-identifies as marker on a fluorescent image including an intensely fluorescent material, a metal, a fluorescent quencher so that the image shows a lack of fluorescence at the point the quencher is applied.

"Nitro" refers to the group —NO$_2$.

"Oxo" refers to the atom (=O) or (—O$^-$).

"Background fluorescence" is generated by, for example, other components of the targeting agent or of the tissue/cells being evaluated that continuously fluoresce, including fluorescent amino acids associated therewith. Such other components will fluoresce regardless of whether the fluorescent moieties attached to the targeting agent are masked (pro-fluorescent) or unmasked (fluorescent) and as such are considered background fluorescence.

"Pro-fluorescent moieties" refer to fluorescein based fluorescent molecules that are reversibly modified to be in a non-fluorescent state and which can be covalently linked to the targeting moiety. As noted above, intracellular conditions are capable of reversing the non-fluorescent state to a fluorescent state.

The term "fluorescein based fluorescent molecules" comprise the core structure of:

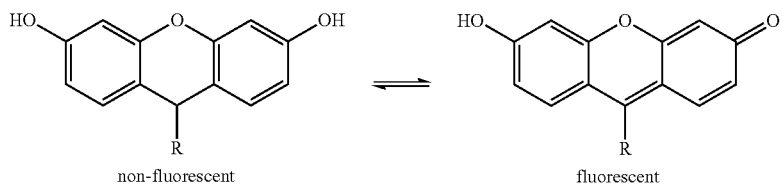

non-fluorescent ⇌ fluorescent where R is cycloalkenyl, substituted cycloalkenyl, phenyl, substituted phenyl and the like. Examples of suitable fluorescein based fluorescent molecules include the following:

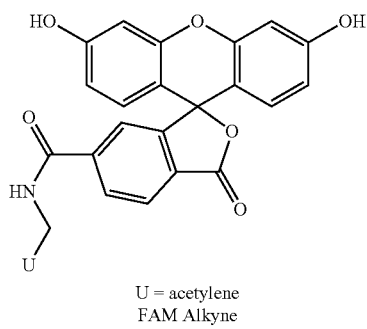

U = acetylene
FAM Alkyne

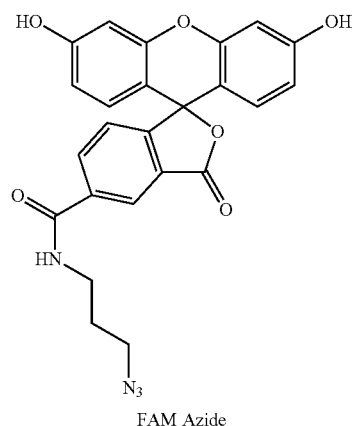

FAM Azide

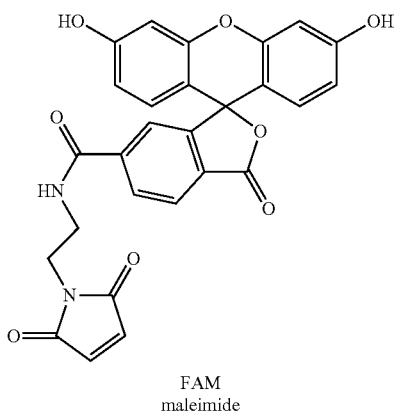

FAM maleimide

-continued

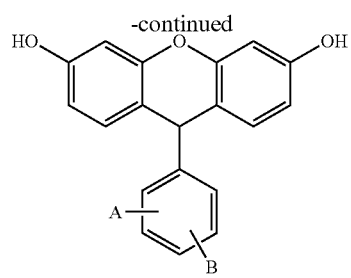

1. A = H; B = 2-COOH
2. A = H; B = 2-methyl
3. A = 4-methyl; B = 2-methyl
4. A = 5-methyl; B = 2-methyl
5. A = H; B = 2-methoxy
6. A = 4-methoxy; B = 2 methyl
7. A = 5-methyl; B = 2-methoxy
8. A = 4-methoxy; B = 2-methoxy
9. A = 5-methoxy; B = 2-methoxy These compounds are tautomers and the non-fluorescent tautomer can be locked into that tautomeric form by esterification of the two phenolic alcohol groups. Removal of one or both of these esters permits the fluorescent tautomeric form to reappear and provide a fluorescent signal.

Non-limiting examples of pro-fluorescent fluorescein based moieties include fluorescein compounds of the formula:

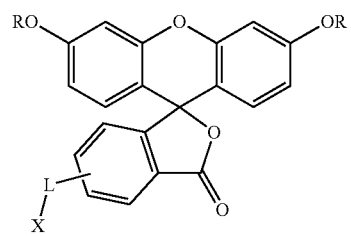

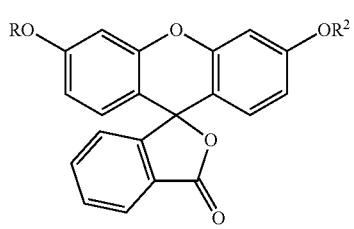

where each R is independently selected from —C(O)R$^1$ and —C(O)NHR$^1$ where R$^1$ is alkyl or substituted alkyl optionally of from 4 to 30 carbon atoms or 5 to 20 carbon atoms; R$^2$ is alkyl, substituted alkyl, alkyl-X, or substituted alkyl-X; L is a covalent bond or a linker having from 1 to 20 atoms selected from the group consisting of oxygen, carbon (e.g., methylene units, methyl, etc), carbonyl, nitrogen, sulfur, sulfinyl, and sulfonyl; X is a suitable group capable of reacting with a complementary functional group on a targeting moiety. Suitable X groups are preferably hydroxyl, amino, substituted amino, thiol, and the like.

Stereoisomers of compounds (also known as optical isomers) include all chiral, d,l stereoisomeric, and racemic forms of a structure, unless the specific stereochemistry is expressly indicated. Thus, compounds used in this invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of this invention.

The compounds of this invention may exist as solvates, especially hydrates. Hydrates may form during manufacture of the compounds or compositions comprising the compounds, or hydrates may form over time due to the hygroscopic nature of the compounds. Compounds of this invention may exist as organic solvates as well, including DMF, ether, and alcohol solvates among others. The identification and preparation of any particular solvate is within the skill of the ordinary artisan of synthetic organic or medicinal chemistry.

"Subject" refers to a mammal. The mammal can be a human or non-human animal mammalian organism.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-. Similarly, "alkylenephenylene" refers to the group (alkylene)-(phenylene)-; and the group "phenylenealkylene" refers to the group (phenylene)-(alkylene)-.

A digital image or picture may comprise red, green, blue pixels or combinations thereof, which pixels or combination of pixels can make up the full color spectrum in said digital image or picture. In some embodiments, said digital image can be a high definition image. Thus, in the context of digital images, the terms "red pixel," "green pixel," and "blue pixel" respectively refer to one of the three basic color pixels that are used to make up the full color spectrum possibly shown in a digital image or picture.

"Digital image" or "digital picture" as used herein refers to a collection of digital information that can be shown on a displaying device, such as a screen. In some embodiments, a digital image or picture is shown on a screen in a surgical environment.

As used herein, the term "pixel-by-pixel" in the context of evaluating or analyzing a digital image encompasses: i) the embodiments where individual pixels in the image are analyzed one by one; and ii) the embodiments where individual groups of pixels in the image are analyzed one by one. In some embodiments, the pixels or groups of pixels collectively make up the entire image. In other embodiments, the pixels or groups of pixels collectively make up a portion of the image.

It is understood that in all substituted groups defined above, polymers arrived at by defining substituents with further substituents to themselves (e.g., substituted aryl having a substituted aryl group as a sub stituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

Conjugates for use in the Methods of the Invention

The compounds used in the methods of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, N.Y., 1999, and references cited therein.

If the compounds of this invention contain one or more chiral centers, such compounds can be prepared or isolated as pure stereoisomers, i.e., as individual enantiomers or d(l) stereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

This invention is directed to methods of using folic or pteroic acid conjugates with a pro-fluorescent fluorescein based moiety optionally via a linker to detect cancer cells. It is being understood that pteroic acid (folic acid without the glutamic acid residue) is recognized by folic acid receptors on numerous different cancer cells.

In some embodiments, the pro-fluorescent fluorescein based moiety is derived by coupling compounds of formula set forth below to folic or pteroic acid:

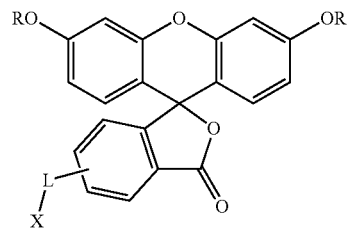

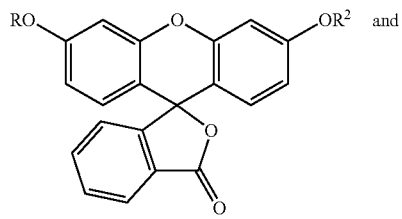
and

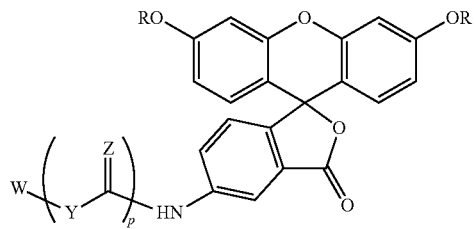

where p is zero or 1; each R is independently selected from —C(O)R$^1$ and —C(O)NHR$^1$ where R$^1$ is alkyl or substituted alkyl optionally of from 4 to 30 carbon atoms or 5 to 20 carbon atoms; R$^2$ is alkyl, substituted alkyl, alkyl-X, or substituted alkyl-X; L is a covalent bond or a linker having from 1 to 20 atoms selected from the group consisting of oxygen, carbon, carbonyl, nitrogen, sulfur, sulfinyl, and sulfonyl; X is a suitable group capable of reacting with a complementary functional group on a targeting moiety; W is alkylene-X or substituted alkylene-X; Y is a bond, CH$_2$, O or NR$^{10}$ where R$^{10}$ is hydrogen or alkyl of from 1 to 6 carbon atoms; and Z is oxygen or sulfur. In one embodiment, X is amino, substituted amino, hydroxyl, thiol, and the like.

Such compounds are numbered as follows:

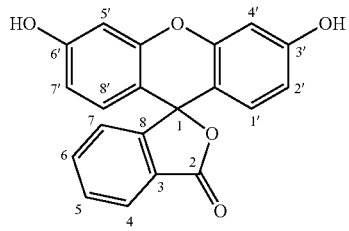

The starting materials for the pro-fluorescent fluorescein based moiety are readily prepared by reaction of one or more 5-aminofluorescein, 5-isothiocyanate fluorescein, 5-iodoacetylamino fluorescein and the like (all commercially available from Sigma-Aldrich, St. Louis, Mo., USA). Alternatively, the reactions below can use 6-substituted fluorescein compounds also commercially available from Sigma-Aldrich.

Conjugates useful in the methods of this application include those set forth below:

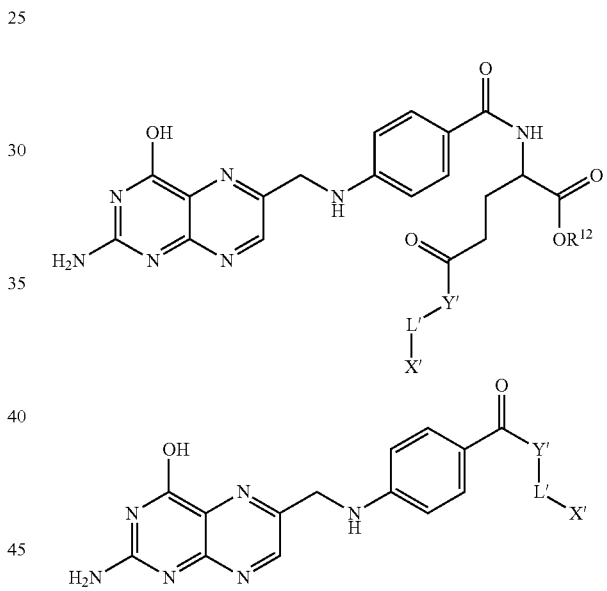

where L' is a bond or a linker having from 1 to 20 atoms selected from the group consisting of oxygen, carbon, carbonyl, nitrogen, sulfur, sulfinyl, and sulfonyl;

X' is a pro-fluorescent fluorescein based moiety;

Y' is —O— or >NR$^{11}$ where R$^{11}$ is hydrogen, C$_1$-C$_6$ alkyl, substituted C$_1$-C$_6$ alkyl; phenyl, substituted phenyl, cycloalkyl, substituted cycloalkyl, heteroaryl, substituted heteroaryl, heterocyclic, substituted heterocyclic; and R$^{12}$ is hydrogen or C$_1$-C$_4$ alkyl;

or salts, tautomers and/or solvates thereof.

In some embodiments, L' is a linker of the formula —NH—R—NH— where R is selected from the group consisting of -(oxyalkylene)$_n$- where n is 1 to 10, alkylene, arylalkylene, arylene, heteroarylene, heterocycloalkylene, alkylenephenylene, phenylenealkylene, and cycloalkylene, each optionally substituted with 1 to 5 substituents selected from the group consisting of alkoxy, substituted alkoxy, amino, substituted amino, acyl, carboxyl, carboxyl esters, cyano, halo, hydroxyl, and thiol.

In some embodiment for folic acid conjugates, these compounds are prepared by first converting folic acid to folic anhydride using methods well known in the art as described by Guaragna, et al., Bioconjugate Chemistry, 2012, 23:84-96 and especially at page 88 and as depicted below in Scheme 2. Specifically, folic acid, compound 3 is combined DCC in a solvent mixture of DMF (dimethylformamide) and pyridine (5:1). The reaction is conducted at a slightly elevated temperature of about 30° C. although the reaction can be run at from about 0° to about 60° C. The reaction is continued until substantially complete and the product, folic anhydride—compound 4, can be recovered by conventional means such as chromatography, distillation, precipitation, high performance liquid chromatography (HPLC) and the like. Alternatively, the product can be used in the next step without purification and/or isolation.

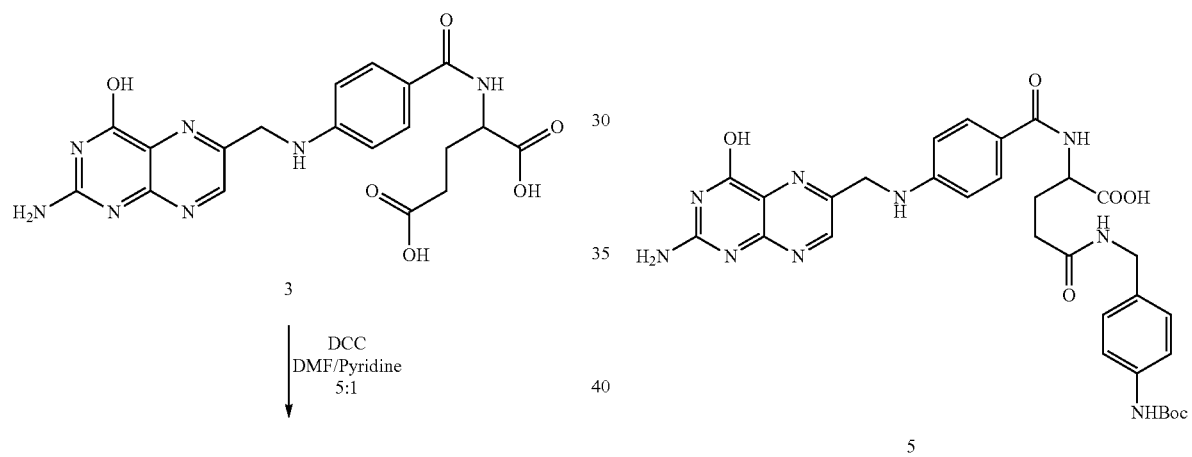

Folic anhydride, compound 4, is next ring opened to form an amide linker moiety, compound 5, as shown in Scheme 3 below:

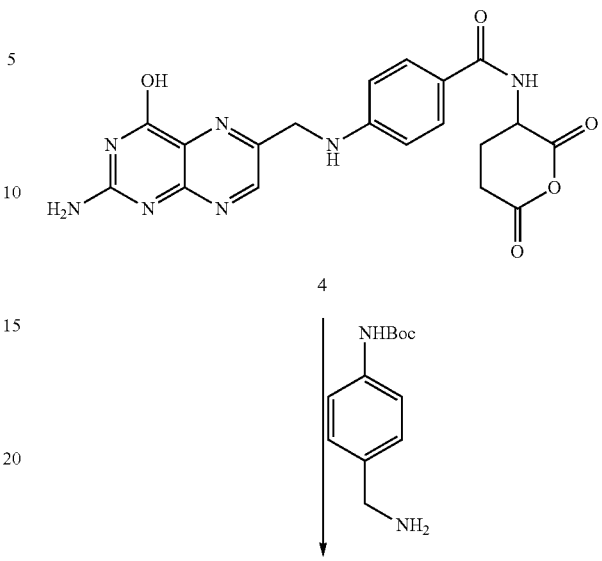

Specifically, commercially available 4-aminomethyl-N-Boc-aniline is combined with folic anhydride, compound 4, together with dicyclohexylcarbodiimide (DCC) under conditions also set forth by by Guaragna, et al., Bioconjugate Chemistry, 2012, 23:84-96 to provide for compound 5. Removal of the Boc (t-butoxycarbonyl) protecting group proceeds via conventional methods using trifluoroacetic acid to provide for the free amino group (compound 6—Scheme 4). The reaction is continued until substantially complete and the product, compound 4, can be recovered by conventional means such as chromatography, distillation, precipitation, HPLC, and the like. Alternatively, the product is used in the next step without purification and/or isolation.

In Scheme 3, the optional inclusion of a $C_1$-$C_4$ alcohol such as methanol leads to the corresponding ester ($R^{12}$=$C_1$-$C_4$ alkyl).

Compound 6 is next linked to compound 2 to form compound (conjugate) 7 as shown in Scheme 4 below:

Scheme 4

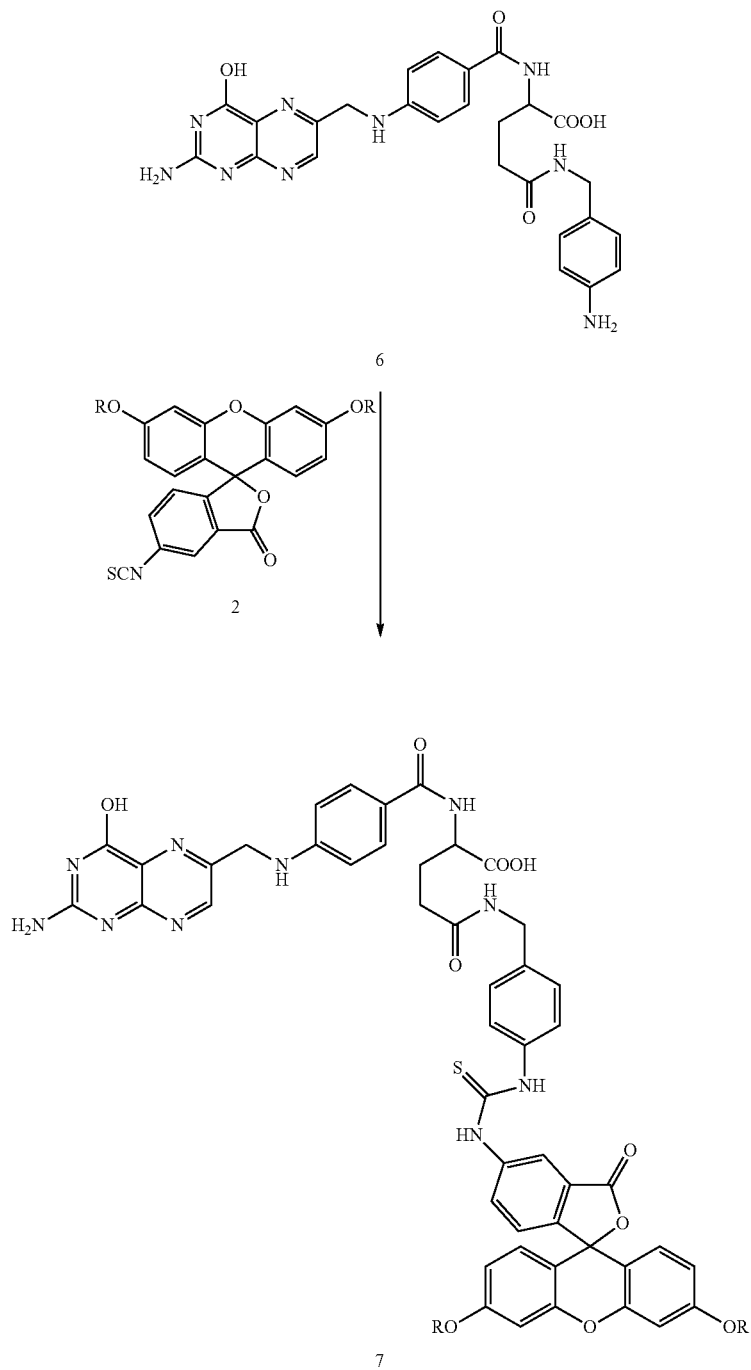

where R is as defined above.

Specifically, compound 2 and compound 6 are combined in a suitable inert aprotic solvent such as dimethylformamide (DMF), acetonitrile, methylene chloride, chloroform, ethyl acetate, tetrahydrofuran and the like. The reaction is typically conducted at from about 0° to about 50° C. for period of time sufficient to substantially complete the reaction and preferably 1 to 24 hours. The reaction completion can be monitored by thin layer chromatography (TLC), high performance liquid chromatography (HPLC), and the product can be recovered by conventional methods such as chromatography, precipitation, crystallization, HPLC, and the like.

The pro-fluorescent fluorescein based moiety is derived by reaction of a reactive form of the pro-fluorescent fluorescein. In one embodiment, such compounds are obtained by formation of an acyl or a carbamyl group off of the hydroxyl groups of a fluorescein compound as shown in Scheme 5 below:

Scheme 5

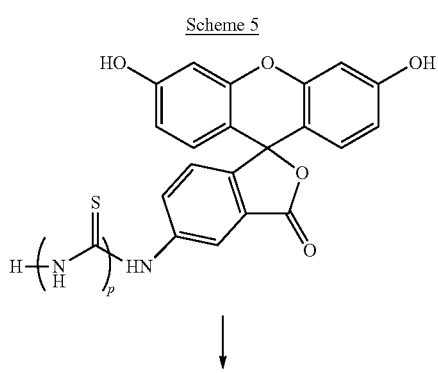

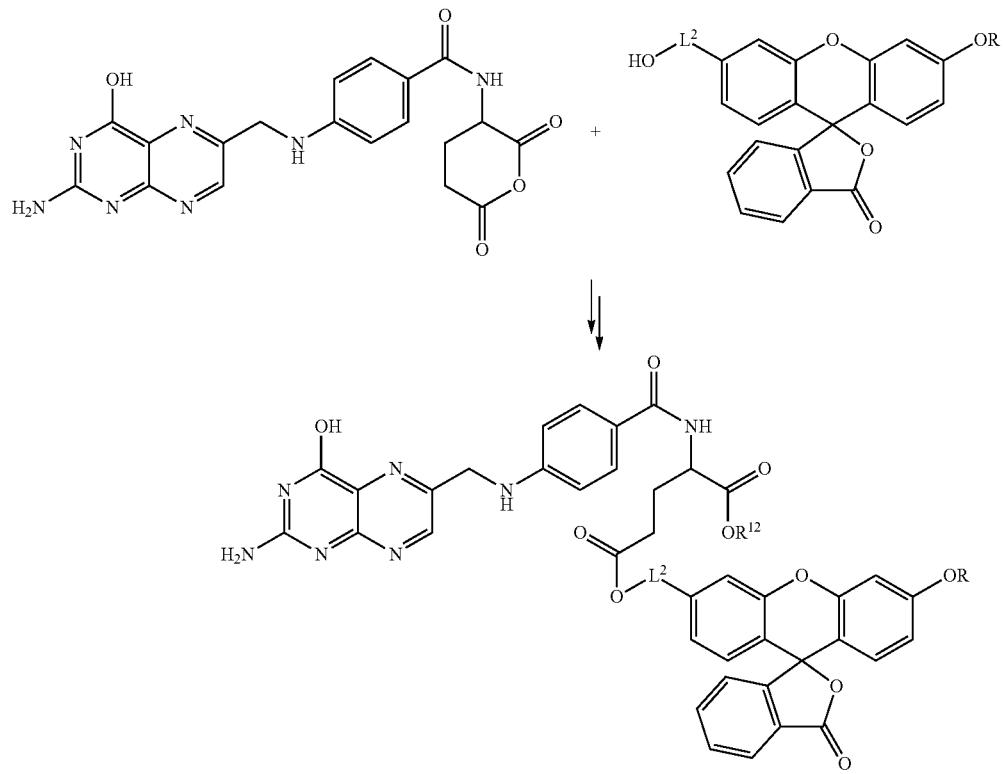

-continued

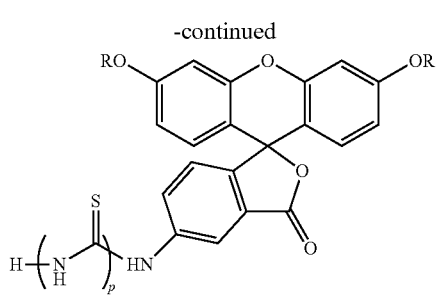

where R is as defined above and p is zero or one.

In Scheme 5, commercially available 5-amino or 5-isothiocyanate fluorescein is readily converted to its corresponding pro-fluorescent structure by conventional formation of an acyl or carbamyl group at the 3',6' positions. The resulting compound is then used as compound 2 in the reactions above.

In the reaction schemes above, fluorescein based compounds can be replaced by non-fluorescein based compounds provided that such compounds are capable of having their fluorescence significantly reduced or eliminated by masking groups.

Still further, linkage of the folic acid to fluorescein can be accomplished through an ether bond formation off of one of the phenolic alcohols as shown below:

where R and $R^{12}$ are as defined above and $L^2$ is -L'-O— where L' is as defined above.

Specifically, in the reaction above, folic anhydride (described above) is combined with fluorescein monoester wherein the remaining hydroxyl group is retained or extended via a linker using conventional techniques. In one embodiment, the linker is a polyoxyalkylene chain of from 1 to 20 units and, in one embodiment, that chain can be represented from left to right as $(CH_2CH_2O)_l$ where l is an integer of from 1 to 20. Introduction of such polyoxyalkylene chains or other linkers is well known in the art. Formation of the ester is also well known in the art and is described above albeit the formation of a sodium phenoxide derivative prior to ester formation will facilitate the reaction. Conversion of the alpha carboxyl group to an ester again proceeds via well known chemistry. In addition, the use of pteroic acid in this reaction in place of folic acid proceeds as above.

Alternatively, pteroic acid can be used in place of folic acid in the above reaction. The reaction conditions are substantially the same and the product is recovered in substantially the same manner. Note that the carboxyl group of pteroic acid will react similarly to the gamma carboxyl group of folic acid.

Examples of compounds useful in the claimed methods include the following:

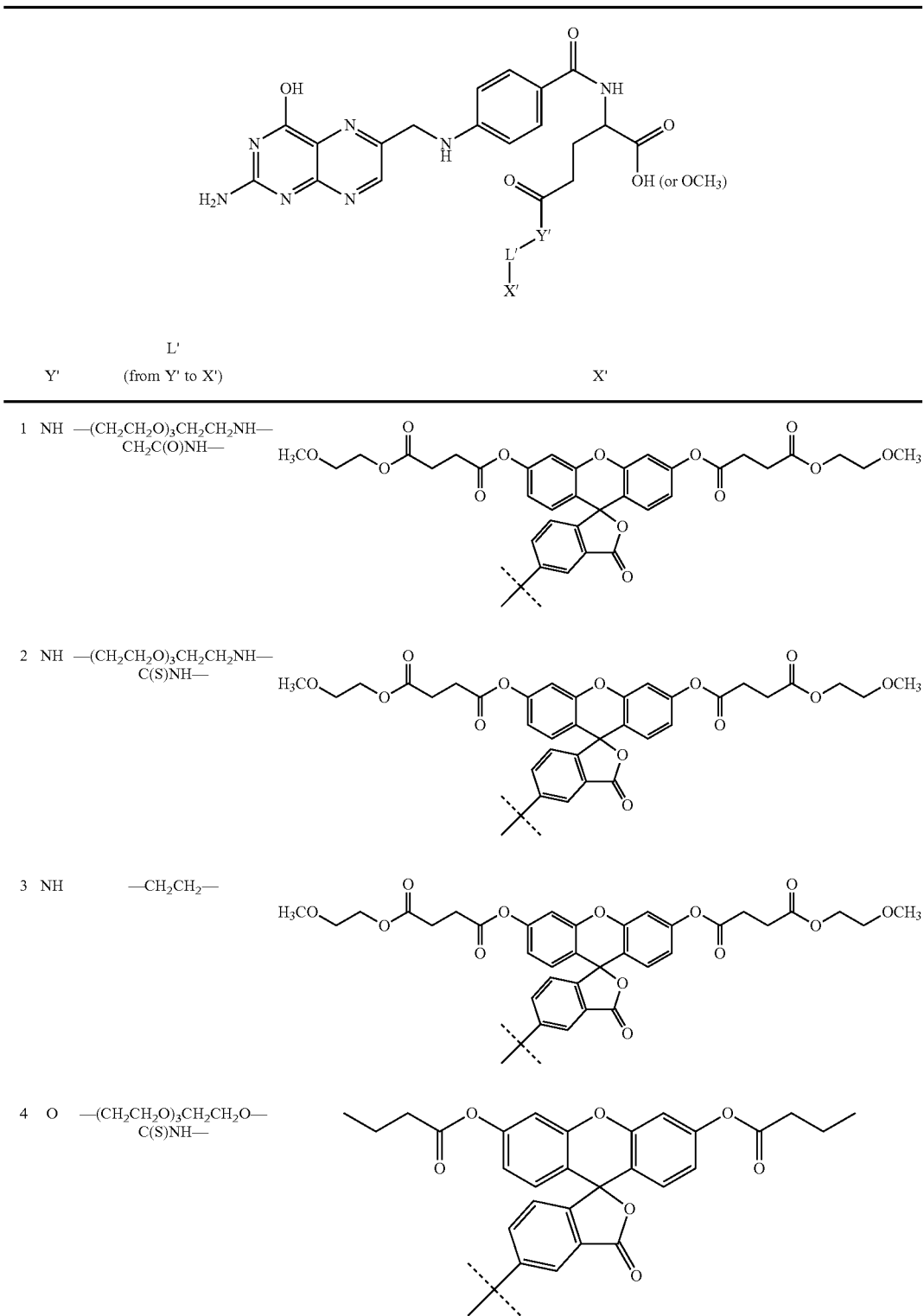

-continued
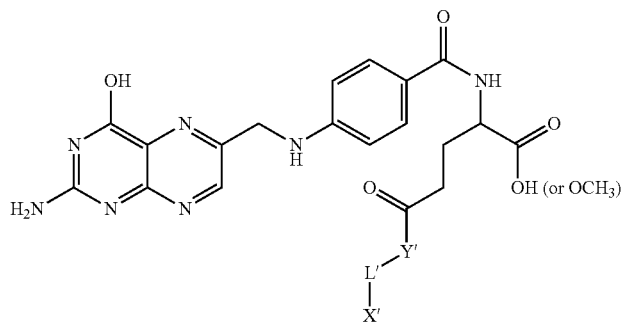
| | Y' | L' (from Y' to X') | X' |
|---|---|---|---|
| 5 | NH | —(CH₂CH₂O)₃CH₂CH₂O—C(S)NH— | 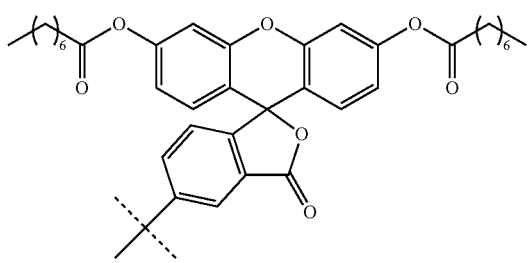 |
| 6 | NH | —CH₂CH₂— | 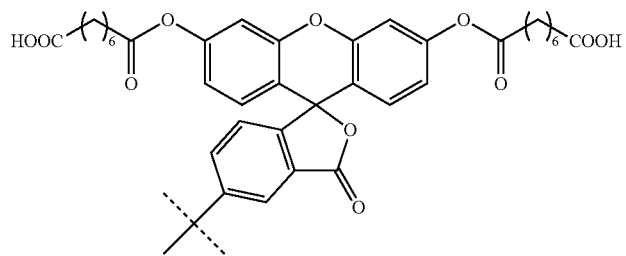 |
| 7 | NH | —(CH₂CH₂O)₃CH₂CH₂NH—CH₂C(O)NH— | 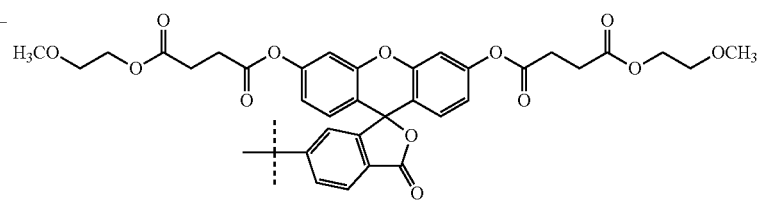 |
| 8 | NH | —(CH₂CH₂O)₃CH₂CH₂NH—C(S)NH— | 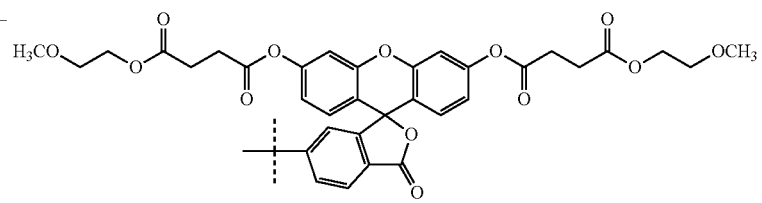 |
| 9 | NH | —CH₂CH₂— | 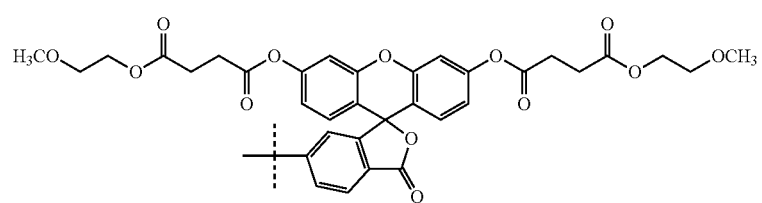 |

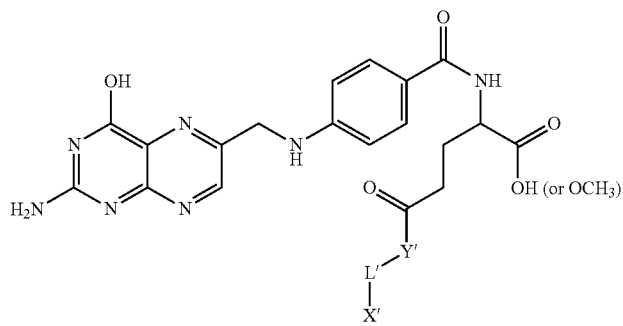
| | Y' | L' (from Y' to X') | X' |
|---|---|---|---|
| 10 | O | —(CH$_2$CH$_2$O)$_3$CH$_2$CH$_2$O—C(S)NH— | 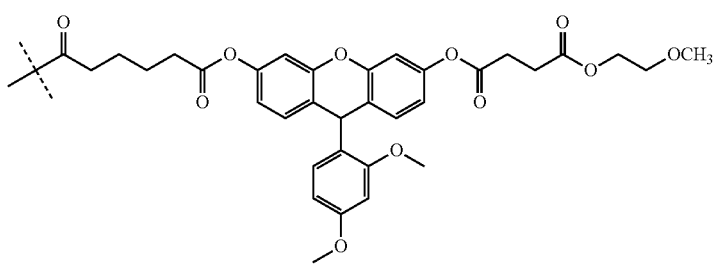 |
| 11 | NH | —(CH$_2$CH$_2$O)$_3$CH$_2$CH$_2$O—C(S)NH— | 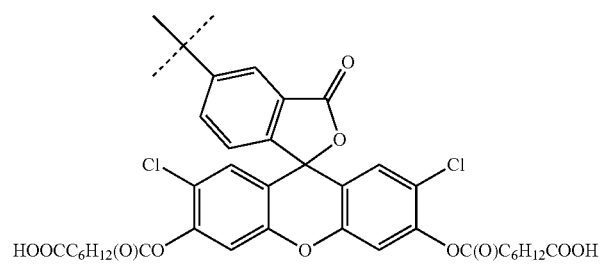 |
| 12 | NH | —(CH$_2$)$_5$— | 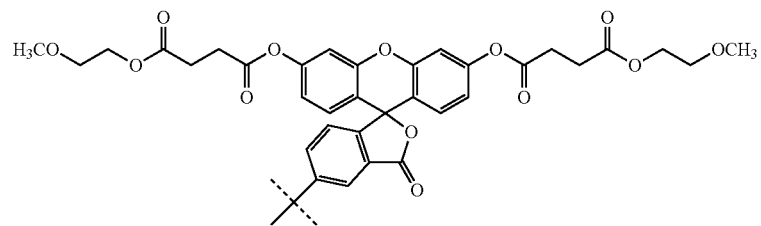 |

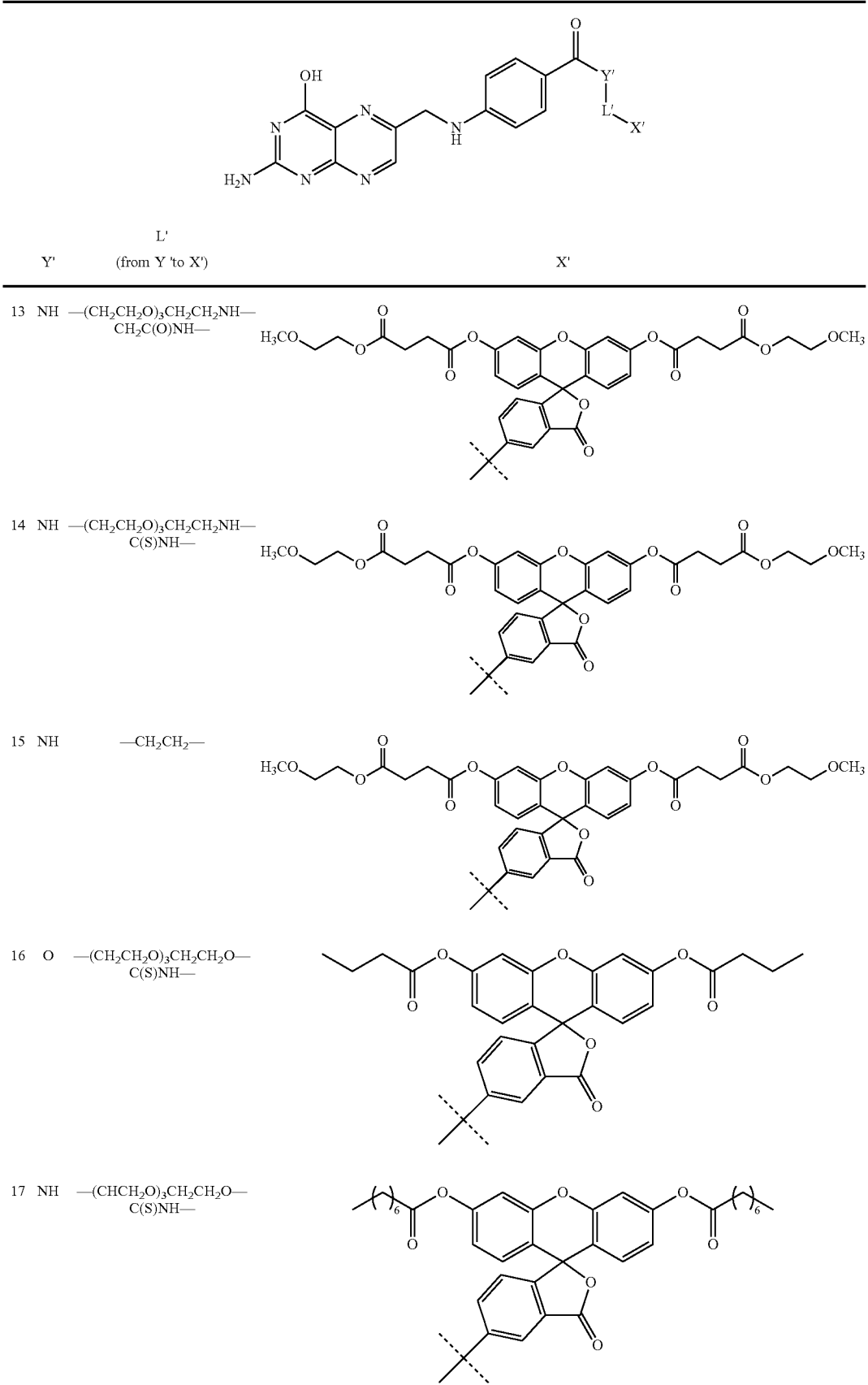

-continued
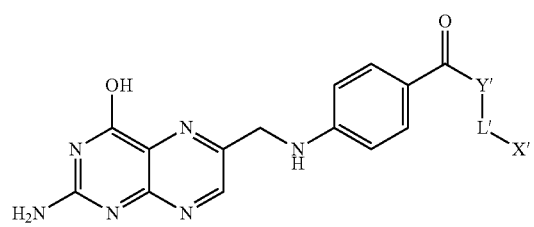
| | Y' | L' (from Y' to X') | X' |
|---|---|---|---|
| 18 | NH | —CH₂CH₂— | |
| 19 | NH | —(CH₂CH₂O)₃CH₂CH₂NH—CH₂C(O)NH— | |
| 20 | NH | —(CH₂CH₂O)₃CH₂CH₂NH—C(S)NH— | |
| 21 | NH | —CH₂CH₂— | |
| 22 | O | —(CH₂CH₂O)₃CH₂CH₂O—C(S)NH— | |

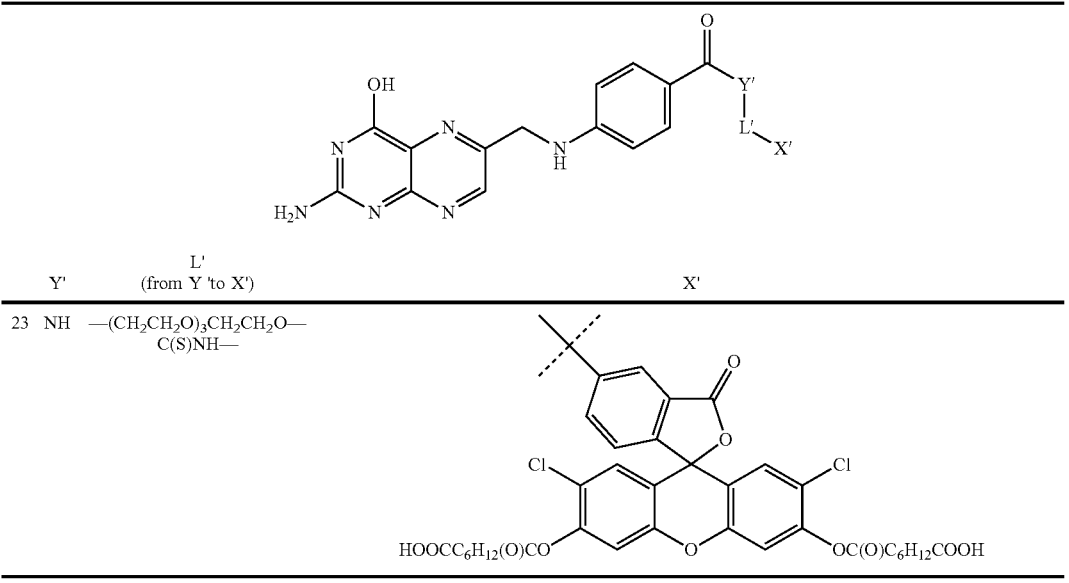

| Y' | L' (from Y' to X') | X' |
|---|---|---|
| 23 NH | —(CH$_2$CH$_2$O)$_3$CH$_2$CH$_2$O—C(S)NH— | |

Methods

This invention provides methods for detecting cancer cells in a tissue sample such as a surgical site after tumor resection or the surface remaining after a dermatologist removes a layer of skin related to basal cell carcinomas. In one embodiment, this invention provides for a method for assessing the presence of cancer cells in a tissue sample suspected of containing cancer cells which method comprises:

a) identifying that portion of fluorescence associated with background fluorescence;

b) measuring total fluorescence in a tissue sample wherein pro-fluorescent moieties are in their fluorescent mode due to absorption coupled with conversion of the pro-fluorescent moieties into fluorescent moieties in said cancer cells;

c) adjusting the total fluorescence to account for background fluorescence to provide for adjusted fluorescence; and d) attributing adjusted fluorescence to cancer cells.

In a), the clinician identifies the background fluorescence due to naturally occurring fluorescent moieties such as the amino acids tyrosine, phenylalanine and tryptophan. Such background fluorescence typically cannot be removed for a variety of reasons. For example, heretofore, the use of pro-fluorescent moieties was not used. Second, many protocols used systemic delivery of a fluorescent moiety bound to a targeting agent. In some cases, this results in off-target binding that provide non-relevant fluorescence. In this invention, the pro-fluorescent moiety avoids background fluorescence as well as off-target binding as such moieties are fluorescent only when absorbed into a cell.

In b), the intracellular pro-fluorescent moieties have been converted to fluorescent moieties and a fluorescent after image is taken of the tissue sample.

In c), the before fluorescent image is compared to the after fluorescent image to differentiate and highlight the fluorescence due solely to the fluorescence generated by the theretofore pro-fluorescent moieties now in their fluorescent state.

In d), the presence or absence of highlighted fluorescence is correlated to the presence or absence of cancer cells in the tissue sample.

In another embodiment, there provided is a method for assessing the presence of cancer cells in a tissue sample suspected of containing cancer cells that overexpress folate receptors which method comprises:

a) evaluating the background fluorescence of said sample to provide for a before fluorescent image;

b) selecting one or more conjugates comprising a targeting moiety wherein said conjugate comprises a folic or pteroic acid targeting moiety covalently coupled to pro-fluorescent fluorescein based moiety optionally through a linker;

c) applying an effective amount of said conjugate to the tissue sample suspected of containing said cancer cells;

d) incubating said tissue sample and said applied conjugate for a sufficient period of time to allow the conjugate to bind to and be absorbed by said cancer cells coupled with conversion of the pro-fluorescent moiety to a moiety capable of fluorescing;

e) assessing fluorescence of the incubated tissue sample to provide for a after fluorescent image;

f) differentiating the before fluorescence image from the after fluorescence image to provide for a differential fluorescent map attributable to cancer cells generating fluorescence from the now fluorescent fluorescein based moieties; and g) attributing said differential fluorescent map to the presence of cancer cells.

In another embodiment, there provided is a method for identifying cancer cells in a cell population suspected of containing cancer cells, normal cells and optionally dead cells, said method comprising:

a) applying an effective amount of a composition comprising a conjugate to said cell population; wherein said conjugate comprises a folic or pteroic acid targeting moiety covalently coupled to pro-fluorescent fluorescein based moiety optionally through a linker;

b) incubating said composition for a sufficient period of time to permit said conjugate to bind to folic acid receptors on said cells coupled with intracellular conversion of said pro-fluorescent moieties to fluorescent moieties;

c) initiating fluorescence within said cell population due to fluorescein;

d) evaluating on a pixel-by-pixel basis intensity of pixels associated with fluorescein fluorescence;

e) discriminating said pixels having less than a first predetermined threshold as background or non-cancerous in nature;

f) discriminating said pixels having more than a second predetermined threshold as arising from the dead cells; and g) altering said discriminated pixels in e) and f) to marker pixels;

h) generating altered image consisting of pixels associated with fluorescein fluorescence that have not been discriminated against; and i) assigning said non-discriminated pixels to cancer cells.

In one embodiment, the before and after fluorescence images are stored electronically and generation of the differential fluorescence map is conducted using appropriate software. Such software preferably evaluates pixel by pixel and differentiates the before fluorescent image from the after fluorescent image to provide a map of differential fluorescence that is attributed to remnant cancer cells.

In another embodiment, the before and after images are taken with one or more markers on the surgical field surface. This allows for the alignment of the before and after images in a manner that allows for accurate differentiation. Preferably, the number of markers ranges from 2 to 10. In some embodiments, the fluorescence is measured in multiple images at different angles so that the surgeon can evaluate an uneven surface as is typical for a tissue sample such as a surgical field.

Kits

The methods of this invention typically employ a composition including by way of example a sprayable aqueous solution including sterile isotonic saline, sterile phosphate buffer saline, and other sterile solutions well known in the art.

As the conjugates may preferably be delivered in solid form, this invention also provides for a kit of parts comprising a solid form of the conjugate, a suitable aqueous diluent in a separate container and a device for applying the resulting composition onto the tissue surface. In one embodiment, the device can be a spray device that provides for an adjustable or fixed spray element. In another embodiment, the device comprises a sponge of other surface applicator that transfers the liquid composition onto the surface of the tissue sample. In another embodiment, the aqueous solution contains a colorant that clearly defines where the composition has been applied to the surgical field. This allows the surgeon to confirm proper application of the composition to the entire surface to be evaluated.

Device

In one embodiment, there are provided devices to practice the methods of this invention. These devices include a UV or NIR light source, a UV or NIR detector for detecting fluorescence, a computer for processing and storing the fluorescent images, and a display device such as a computer monitor or TV screen.

The light source is placed over the surgical field at a reproducible height and reproducible intensity and wavelength output so that each fluorescent image correlates to the other images. For example, light intensity diminishes to the square of the distance from the source such that the intensity of light at a distance of 2 feet from the source is one-fourth that found at 1 foot from the source. Hence, it is necessary to assure that the light source is consistently at the same distance from the surgical field.

Given that the patient is breathing or otherwise might have moved, one example of ensuring that the distance from the surgical field to the light source is identical is to use a laser for accurate measuring to a specific marker on the surgical field. The light source is programmed not to emit light until the laser measurement assures that the distance from the marker is the same as in other images. Laser "tape-measurers" are well known in the art.

Similarly, the detector should be at the same distance from the patient in each image. This can be assured by combining the light source and the detector into the same device.

In one embodiment, the light source and the detector are mounted on a swing arm at a fixed distance from the operating room bed. The light source and detector are side-mounted in a vertical direction in the swing arm so that the vertical distance to the patient can be measured and adjusted. Once the adjustment is made, fluorescent imaging can be conducted.

In order to avoid the UV light source reflection from the surgical field from interfering with the fluorescent image, filters on the light source can be used. For example, the fluorescence generated by fluorescein overlaps in part with its excitation wavelength meaning that reflected excitation light could be misconstrued as fluorescence. The use of an excitation light filter and a filter on the fluorescence detector obviates this concern. In such an instance, an excitation filter allowing only light at, for example, 450 nm or more intense to be applied to the surgical surface while a detection filter at, for example, 550 nm or less intense to be measured would avoid the issue of reflection. Other approaches include measuring fluorescence at a 90 degree angle to the direction of the excitation light. As fluorescence occur in all angles (i.e., 360 degrees), measuring fluorescence at 90 degrees to the direction of the excitation light obviates reflection.

To provide for the proper UV light intensity on the surgical field so as to provide proper fluorescence intensity (neither to weak or too strong), one can merely adjust the height of the swing arm from the operating room bed. The proper adjustments take into account the size of the patient, the label used, and the degree of resolution required. All of these are within the skill of the art.

High-resolution digital cameras capture digital images and store the images on computers. Computer software is then capable of searching the before and after images and determining the differences in fluorescence (differentiation). The camera generated digital images consist of a bitmap of many thousands of pixels in rows and columns; for example 1,000 rows by 1,000 columns equals a million pixels. In typical bitmap image file formats in use, each pixel contains 32 bits, which are separated into four 8 bit bytes. The first byte is not of interest. The remaining three 8 bit bytes (cells) will contain values ranging from 0 to 255, which represent the relative intensity of the three primary colors, red, green, and blue, so that the combination of each cell's color value will determine the color the human eye will see. By using the RGB values, each pixel (cell) can thus have more than 16 million color values, thus allowing for the detection of very small changes in pixel values between before and after images.

Suitable software aligns each image so that each pixel in one image corresponds to the same pixel in the next image. This is achieved by aligning the markers in each image so as to ensure proper overlay of one image to the next. After alignment, the computer detects the differences in pixel colors between the before image used to determine Background Fluorescence and the after images of Reassessed Fluorescence and identifies those pixels that are determined to have significantly increased fluorescence. Once the detection process is complete, three images are available for viewing, the before and after images, plus a third image that is an exact copy of the after fluorescence image with the detected fluoresced pixels highlighted to make them more visible to the naked eye. The images are stored on the computer for subsequent visual comparison, plus the images are transferred to a viewing device such as a computer monitor, a TV screen or any other commonly used devices.

In some embodiments, the computer software is set to have certain threshold values for analyzing an image. In some embodiments, a minimum intensity threshold is set at 35, such that the software discriminates against pixels having an intensity value ≤35. In some embodiments, the software discriminates against pixels having an intensity value in the range of about from 10 to about 35. In some embodiments, the software discriminates against pixels having an intensity value smaller than 30, smaller than 25, smaller than 20, smaller than 15, smaller than 10, or smaller than 10. In some embodiments, pixels having intensity values below the minimum threshold is considered as associating with background fluorescence or cells of non-cancerous nature.

In some embodiments, a maximum intensity threshold is set at 210, such that the software discriminates against pixels having an intensity value ≥210. In some embodiments, the software discriminates against pixels having an intensity value in the range of about 210 to about 255. In some embodiments, the software discriminates against pixels having an intensity value greater than 210, greater than 220, greater than 230, greater than 240, or greater than 250. In some embodiments, pixels having intensity values above the maximum threshold is considered as associating with artifacts or dead cells.

Uses

The methods described herein are useful for detecting cancer cells in a tissue sample. In one embodiment, the tissue sample is a surgical field after resection of a tumor. In another embodiment, the surgical field is tissue remaining after removal of a basal cell carcinoma so as to allow the clinician ready determination if the tissue remaining on the patient still retains any basal cell carcinoma cells. This latter aspect is critical as it allows the clinician confidence that s/he has removed sufficient tissue so as to remove all of the cancerous basal cells.

Still further, this assay can be conducted on the tissue surface after a suspect mole is removed as well as on the removed mole itself so that the clinician can determine if the mole is cancerous or used on biopsied tissue samples.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention. Various modifications of this invention in addition to those described herein will become apparent to those skilled in the art from the foregoing description and accompanying figures. Such modifications fall within the scope of the appended claims.

The following abbreviations are used in the examples below and have the following meanings. If an abbreviation is not defined, it has its art recognized meaning. In addition, all temperatures are in degrees Celcius unless otherwise noted.

DCC=dicyclohexycarbodiimide
DMF=N,N-dimethylformamide
DMAP=N,N-dimethylaminopyridine
DMSO=dimethylsulfoxide
eq.=equivalents
ether=diethyl ether
FBS=fetal bovine serum
mg=milligram
mL=milliliter
mm=millimeter
mM=millimolar
mmoles=millimoles
RPMI=Roswell Park Memorial Institute medium
MP=melting point
RT=room temperature
TFA=trifluoroacetic acid
TLC=thin layer chromatography
μM=micromolar
μm=micromoles
V/V=volume/volume Example 1—Synthesis of 2-(4-(((2-amino-4-oxo-3,4dihydropteridin-6-yl)methyl)amino)benzamido)-5-((3'6'-dihydroxy-3-oxo-3H-spiro[isobenzofuran-1,9'-xanthen]-5-yl)amino-5-oxopentanoic Acid (Compound 13)
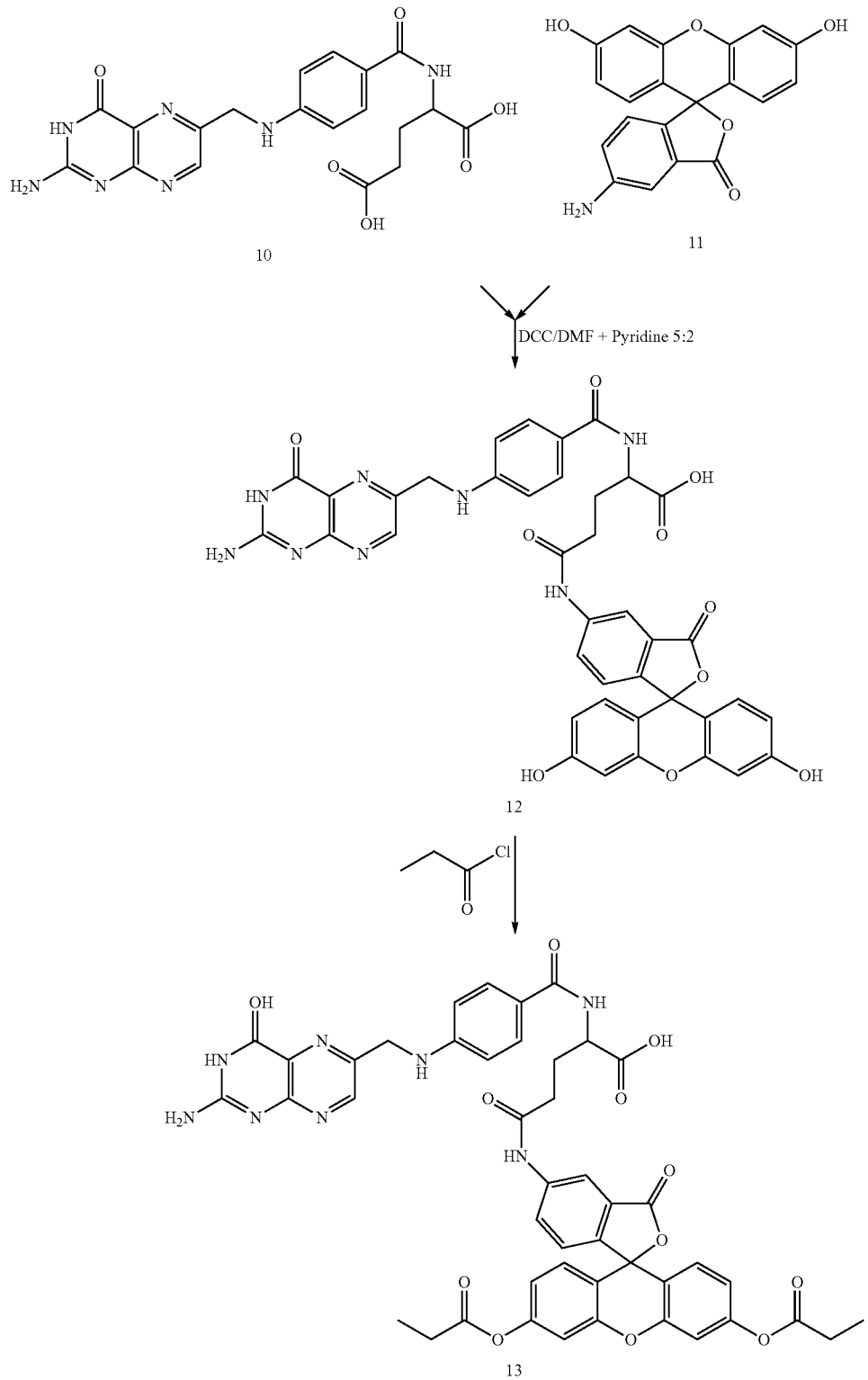

A mixture of 100 mg (0.22 mmoles) folic acid (compound 10) in an anhydrous 20 mL DMF solution plus 4 mL pyridine was heated and vigorously shaken to get a clear golden solution. To this solution was added 6 equivalents of DCC (0.280 mg, 1.36 mmoles). The reaction mixture was mixed in an ultrasound bath in the dark for 15 minutes twice, while the bath warmed to about 29° C. The resulting cloudy solution was added to a flask containing 1.1 equivalents 5-aminofluorescein (86.5 mg, 0.249 moles) (compound 11). The resulting reaction mixture was wrapped with aluminum foil and stirred at room temperature overnight. After about 18 hours the mixture was filtered through celite and added drop-wise to a mixture of 70 mL ether and 30 mL acetone. The cloudy mixture was stored in the dark in a freezer for several days. The solid (compound 12) was filtered off, washed with ether and air-dried to a constant mass of 115.7 mg (66.3%).

29.4 mg of the folic acid-fluorescein conjugate (compound 12) was dissolved in 2 mL dry DMF, and 6 equivalents (23.6 mg) triethylamine was added, followed by 5 equivalents of propionyl chloride (17.6 mg). The reaction was stirred at room temperature for several days, and poured into a mixture of water and ethyl acetate. The organic layer was washed with water and brine and dried over sodium sulfate. After evaporation of the solvent the solid was further dried to yield 20.6 mg (54%). MP: >290°. Confirmation of the product was further provided by loss of fluorescence due to the diesterification of the fluorescein phenolic hydroxyl groups of compound 13. Specifically, when a sample of compound 13 was dissolved in methanol a non-fluoresecent solution resulted. On treatment with a few drops of ammonia water intense fluorescence was noted. The ammonia is a strong deacylating agent that unmasks the masked fluorescent fluorescein diester.

Example 2—Synthesis of O,O'-(5-(3-(4-((4-(4-(((2-amino-4-oxo-3,4-dihydropteridin-6-yl)methyl)amino)benzamido)-5-methoxy-5-oxopentanamido)methyl)phenyl)thioureido)-3-oxo-3H-spiro[isobenzofuran-1,9'-xanthene]-3',6'-diyl) bis)(2-methoxyethyl) Disuccinate (Compound 18)

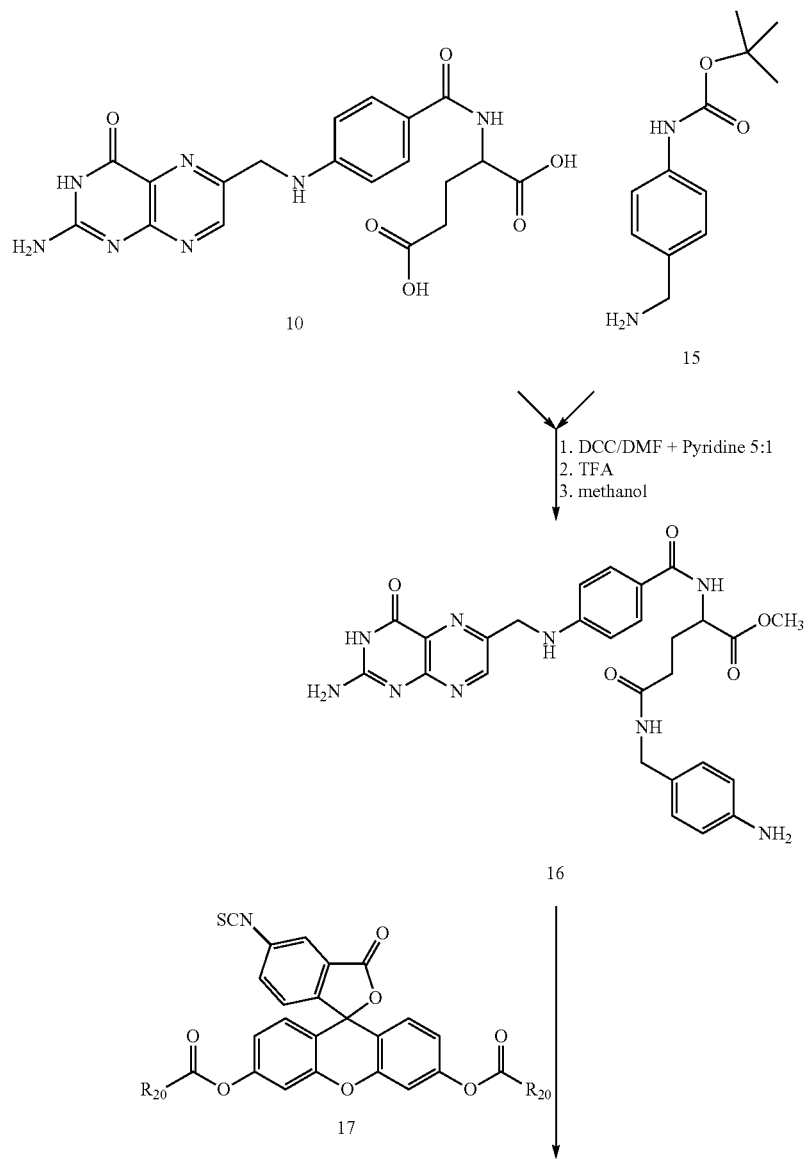

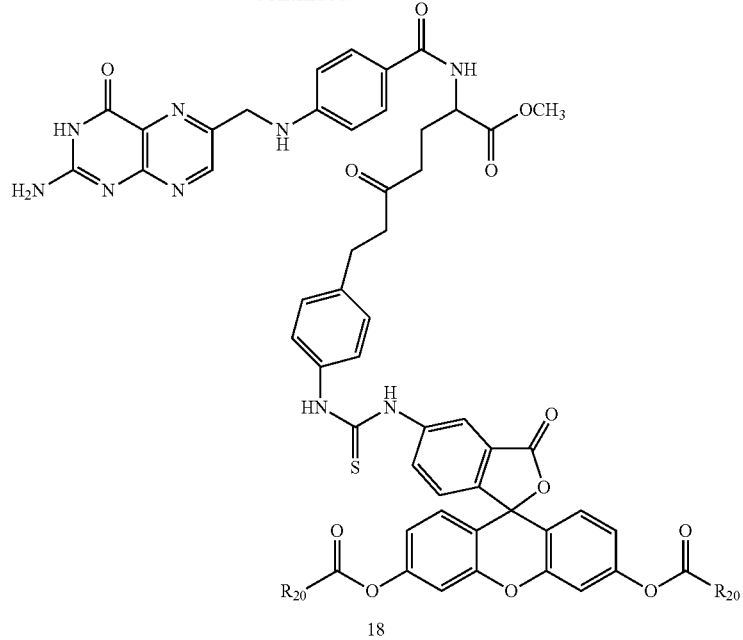

18

A. Synthesis of O,O'-5-isothiocyanato-3-oxo-3H-spiro[isobenzofuran-1,9'-xanthene]-3',6'-diyl) bis(2-methoxyethyl)disuccinate (Compound 17)

A1.

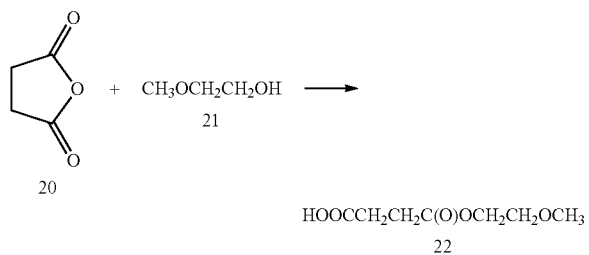

The above reaction follows the literature preparation described by J. Materials Chemistry, 2014, 2(26):4142-4145. Specifically, a slight excess of succinic anhydride was combined with 2-methoxyethanol in methylene chloride in a flask at about 20° C. A solution of triethylamine in methylene chloride was added dropwise over about a 15 minute period during which the reaction produced sufficient heat so that the solvent began to boil. Afterwards, the addition of triethylamine was stopped and the reaction stirred overnight after returning to room temperature. The reaction was stopped and the reaction solution washed with brine and the organic layer was recovered. The solvent was stripped and the resulting product was purified by column chromatography (silica gel using a gradient of from 0 to 10% methanol in methylene chloride v/v). The resulting product (compound 12) was used as is without further purification or isolation.

A2

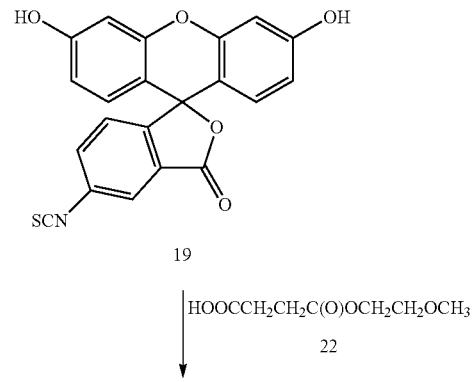

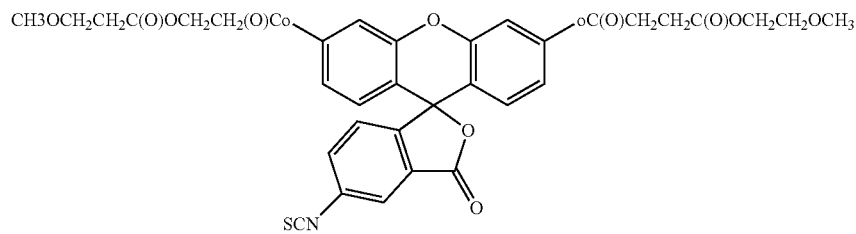

17

Approximately 1 eq. of compound 22 was dissolved in methylene chloride and then combined with approximately 1 eq. of DCC at room temperature. The mixture was stirred for approximately 5 minutes and then 0.25 equivalents of DMAP and approximately 0.25 eq. of fluorescein were added thereto. The reaction mixture was then sonicated at 26° C. until the suspension was substantially dissipated which occurred over approximately 15 minutes. The resulting reaction mixture was stirred overnight at room temperature and monitored for reaction completion by TLC. Upon substantial reaction completion, the non-soluble components were filtered and the resulting solution was placed on a silica column for purification purposes. The column was eluted with a solvent gradient starting at 0% methanol and 100% methylene chloride and finishing with 10% methanol and 90% methylene chloride (v/v). The elutant containing the desired compound was stripped of solvent and the resulting compound 14 was substantially free of fluorescence indicative of formation of diester. A small aliquot of the compound was contacted with a sodium hydroxide solution that immediately provided for fluorescence indicative of deacylation. The sodium hydroxide is a strong deacylating agent that unmasks the masked fluorescent fluorescein diester.

A3

A mixture of 100 mg (0.22 mmoles) folic acid (compound 10) in an anhydrous 20 mL DMF solution plus 4 mL pyridine was heated and vigorously shaken to get a clear golden solution. To this solution was added 6 equivalents of DCC (280 mg, 1.36 mmoles). The reaction mixture was mixed in an ultrasound bath in the dark for 15 minutes twice, while the bath warmed to 29° C. The resulting cloudy solution was added to a flask containing 1.1 eq. tert-butyl (4-aminomethyl)phenyl)-carbamate (58.3 mg) (compound 15). The resulting reaction mixture was wrapped with aluminum foil and stirred at room temperature overnight. After about 18 hours 1 mL of methanol was added to esterify the alpha-carboxylic acid (this is an optional step). After stirring for an additional 24 hours at RT, the mixture was filtered through celite and added drop-wise to a mixture of 70 mL ether and 30 mL acetone. The cloudy mixture was stored in the dark in a freezer for several days. The solid was filtered off, washed with ether and air-dried to a constant mass of 72 mg (48.2%). Without further purification, 24 mg of this compound was added to 0.5 mL TFA (large excess) stirred at room temperature and then stored in the refrigerator. The TFA was evaporated to yield 20 mg (35.7 μm) of compound 16. This material was then dissolved in a small amount of DMF and treated with 1 equivalent (25 mg) of compound 17. The reaction was stirred at room temperature overnight. The mixture was added to a large amount of ether (75 mL) to yield a precipitate, which was filtered off, washed with ether and dried to 29 mg (64%) of a tan solid, MP: softens at 200° C. and melts at 216-226° C. (compound 18) A small sample of this material was dissolved in methanol yielding a clear colorless solution. When a few drops of ammonia water were added, the solution became intensely fluorescent. The ammonia is a strong deacylating agent that unmasks the masked fluorescent fluorescein diester.

Comparative Example A
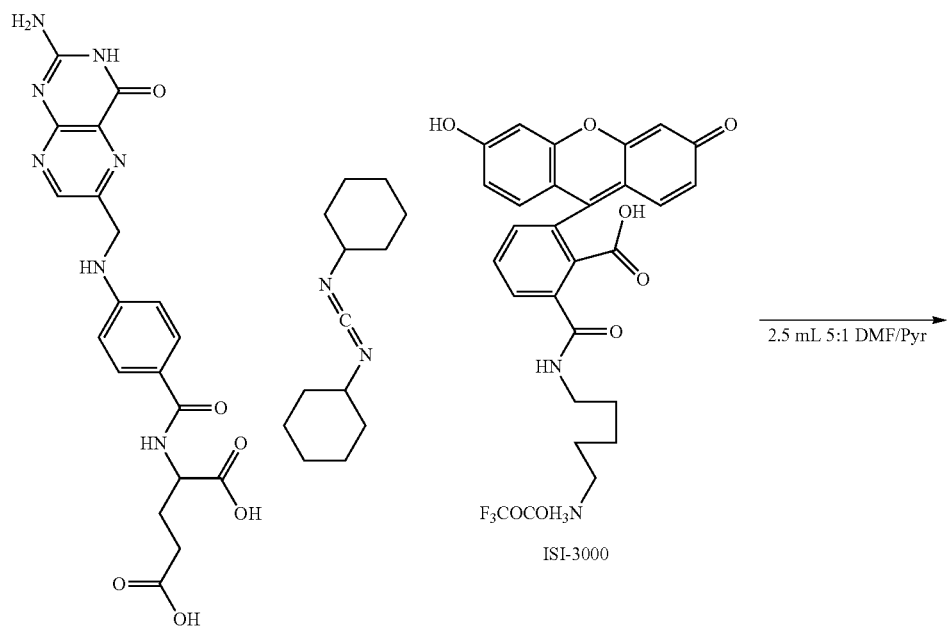
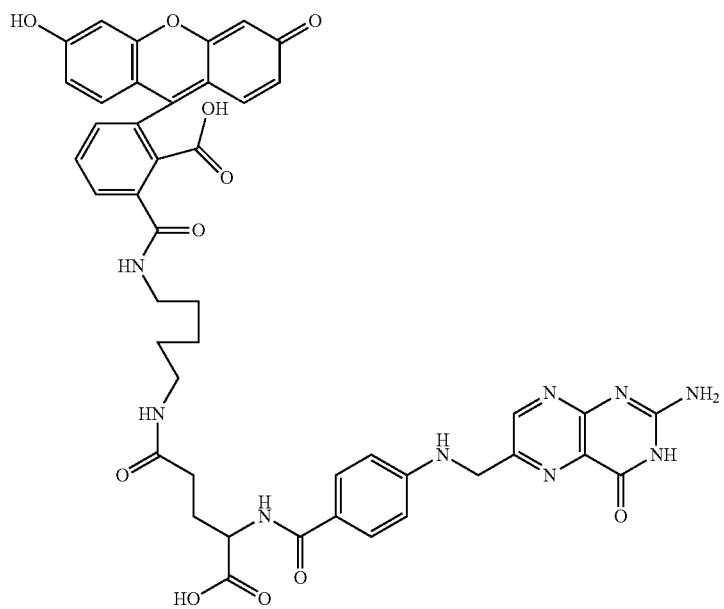
25
MP: Lost red color over 220°
MP > 290°.
Compound 25 was prepared following the procedures set forth above ad provided for the title compound as a comparative example (no ester groups on the fluorescein moiety).

Example 3—Synthesis of the Fluorescein Diester, Compound 26

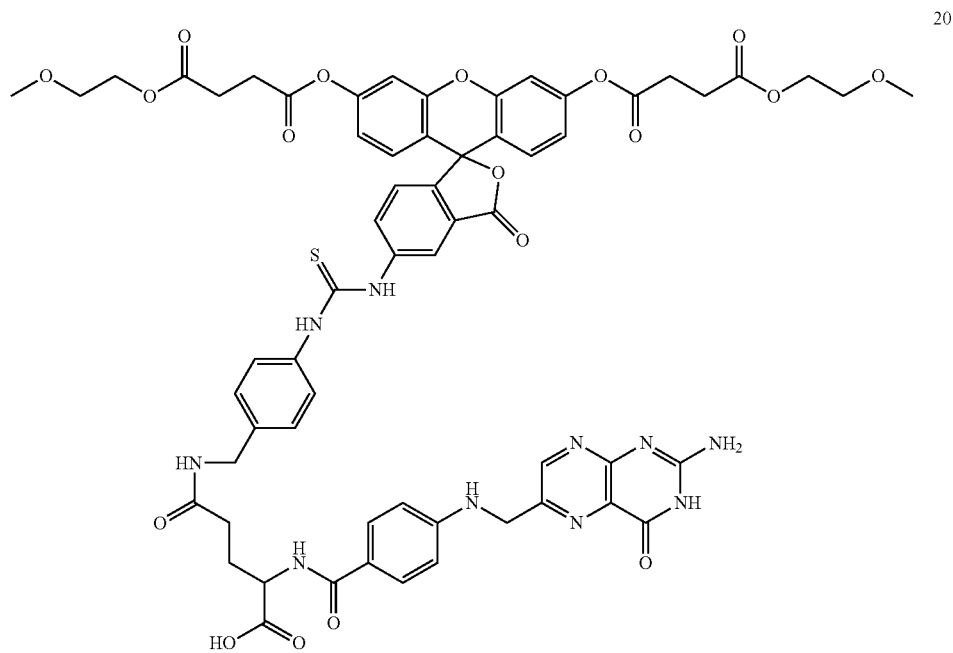

Following the procedure of Example 2 and omitting the addition of methanol, compound 20 is prepared. When a sample of compound 13 was dissolved in methanol, a non-fluoresecent solution resulted. On treatment with a few drops of ammonia water intense fluorescence was noted. The ammonia is a strong deacylating agent that unmasks the masked fluorescent fluorescein diester.

Example 4—Synthesis of the Fluorescein Diester, Compound 27

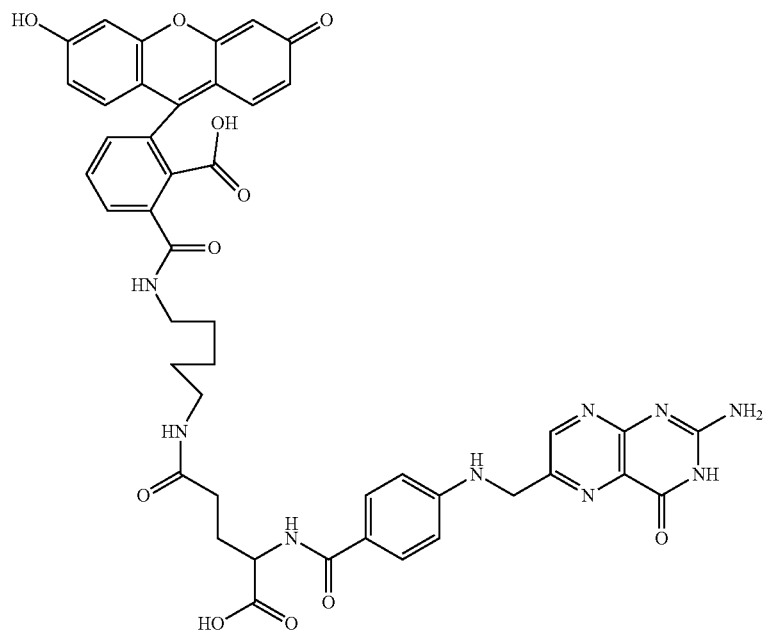

-continued

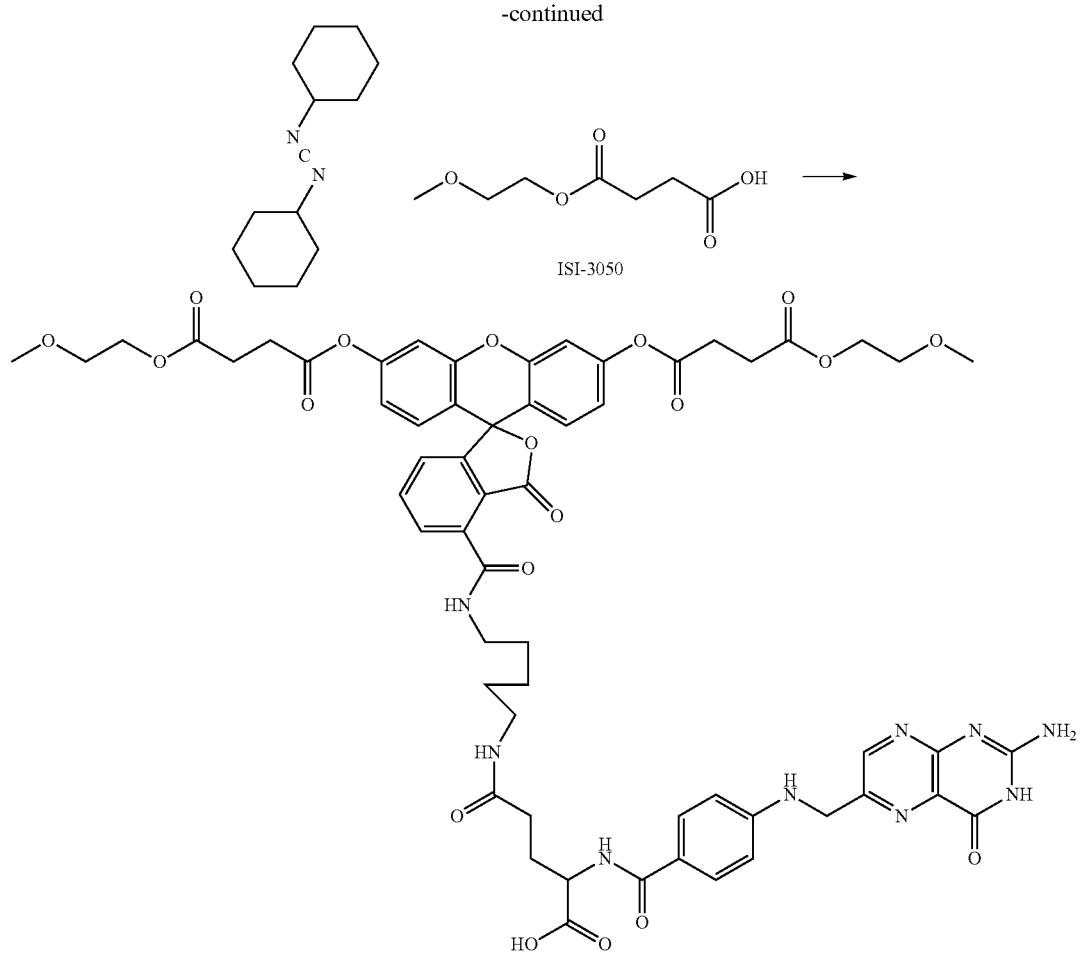

MP: became red > 165°
melted 193-196°.
27

Compound 27 was prepared following the procedures set forth above. Specifically, when a sample of compound 13 was dissolved in methanol a non-fluorescent solution resulted. On treatment with a few drops of ammonia water intense fluorescence was noted. The ammonia is a strong deacylating agent that unmasks the masked fluorescent fluorescein diester.

Example 5—Synthesis of Pteroic Acid Derivative

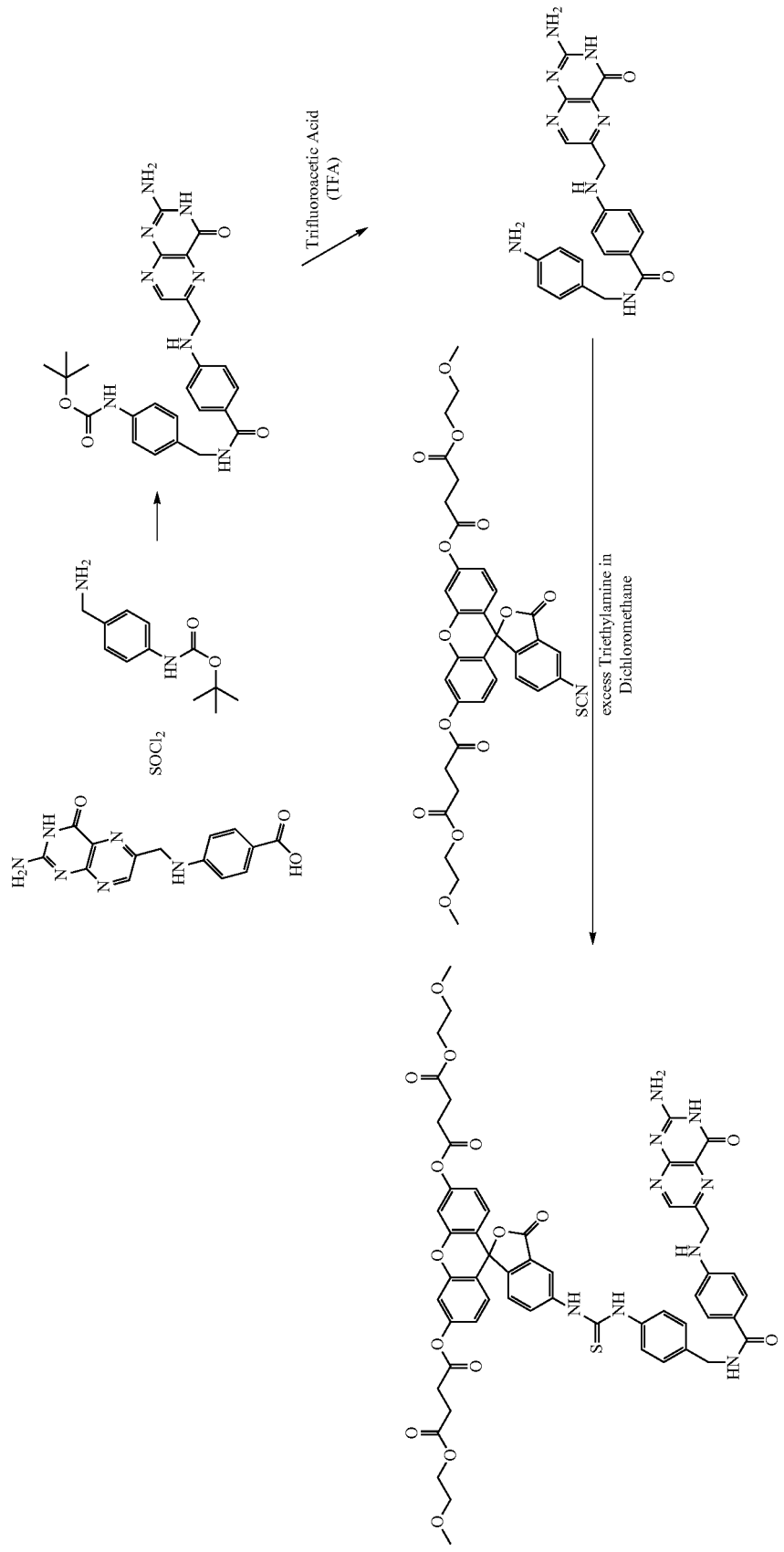

12 mg of pteroic acid (Sigma Aldrich, St. Louis, Mo., USA) was mixed with about 1.5 mL of DMF, and heated to about 80° C. with stirring for a few minutes. The pteroic acid did not go into solution. The mixture was then cooled to RT and excess thionyl chloride was added and a clear solution was generated almost immediately indicating the formation of the acid chloride. 8.2 mg 4-(aminomethyl) t-Boc-aniline was added and the clear solution stirred overnight. The clear golden-colored solution was treated with a few drops of triethylamine and the solution became very dark and viscous. After stirring for 3 hours, the solution was added to 50 mL of ether using several milliliters of acetone in the transfer. The precipitate was filtered and was dark and wet. It was treated with charcoal and washed through the funnel with DMF and then acetone. The filtrate was again added to 50 mL of ether and a lighter colored precipitate formed. The mixture was stored in a refrigerator overnight. The solid was filtered off and treated with excess trifluoroacetic acid (TFA) to remove the Boc group. Dichloromethane was used as the solvent. The excess TFA was removed under vacuum and the residue was dissolved in dichloromethane and excess triethylamine added until the solution was basic. To this solution was added excess fluorescein 5-isothiocyanate diester (as depicted in the scheme above) in dichloromethane. The reaction was then stirred at room temperature. The solution was then added to 10 mL of ether that was then cooled in ice. The solid was collected after centrifuging and transferring to a glass fritted filter funnel, washed with excess ether, and air-dried. About 8 mg of the product was obtained as a dark solid.

MP=155-158° C.

To confirm that the product contained the fluorescein diester moiety, a sample of the product was dissolved in methanol to provide a clear amber solution with no evidence of fluorescein fluorescence. Upon addition of aqueous ammonia, an intense characteristic yellow-green fluorescence was obtained.

Biological Examples

A. Detection of Ovarian Cancer Cells

Compound 24 and comparative compound A were evaluated for their ability to be absorbed by cancer cells and then, in the case of compound 24, deacylated by intracellular esterases so as to regenerate a fluorescent structure. Specifically, approximately 500,000 SDOV3 cells (an ovarian cancer cell line) were seeded into separate 35 mm culture dishes containing a folate-free growth medium (RPMI+10% FBS). The next day, the medium was replaced with a folate-free medium (no FBS). In one culture dish, the medium was supplemented with 25 micromolar of compound 24; and, in another culture dish, the medium was supplemented with 50 micromolar of comparative compound A. After incubation, the cells were washed with HBSS (Hank's balanced salt solution) to remove unbound compound. The cells were then imaged with a 20× immersion objective on a standard upright fluorescent microscope. In the case of compound 24, the fluorescent signal was clear, consistent and unambiguous evidencing that cancer cells were fluorescent and that the fluorescent signal was not evident in the solution. FIG. 1 illustrates a picture showing the fluorescence generated. Note that only the cancer cells evidenced fluorescence and that the solution remained non-fluorescent. As to comparative compound A, that solution showed a burst of fluorescence but immediately the fluorescence was bleached and the composition no longer was capable of fluorescing. This evidences that that composition was not suitable for use in the methods described herein.

These results establish that compound 24 targeted cancer cells, were absorbed by cancer cells, and were deacylated by intracellular enzymes. The persistent signaling solely in the cancer cells evidenced that deacylated compound 24 did not efflux from the cancer cells. On the other hand, comparative compound A also was absorbed by the cancer cells and immediately fluoresced but that was followed by loss of fluorescence likely due to bleaching under the intense light used.

Taken together, the compounds of this invention are suitable for use in detecting remnant cancer cells. Because certain cancer cells preferentially uptake the conjugates of this invention, after incubation for a period of time, removal of the applied solution from the surgical field will limit absorption into normal cells. Such can be accomplished under conventional lavage/washing conditions.

B. Detection of Ovarian Cancer Cells is via the Folic Acid Receptor

This example establishes that compound 24 is specific for the folate receptor. Specifically, compound 24 was used in a folate free medium and in a medium using excess folate that competed with compound 24. The rationale is that in the presence of excess folate, compound 24 would have to compete for binding to the folate binding protein and therefore there would be less signal than when compound 24 was the sole source of folate.

To test this hypothesis, SKOV3 cells were incubated with 10 μM of compound 24 or with 10 μM of compound 24+1 mM folate (100×s). Cells were then washed and imaged as before.

All images were analyzed using exactly the same parameters. Mean intensity was measured from identical regions with in each image. Images, shown in FIGS. 2A and 2B, clearly indicate that folate competes with compound 24 for labeling ovarian cancer cells. These images establish that compound 24 binds to cells through the folate binding protein and not by some other route.

C. Dose Response

This experiment establishes that compound 24 provides a dose response relative to the fluorescence generated. Specifically, SKOV3 cells were incubated with 10 μM, 25 μM, or 50 μM of compound 24 in RPMI supplemented with 0.25% BSA. Cells were incubated for 1 hour then washed with HBSS and imaged as before.

All images were analyzed using exactly the same parameters using the image J software suite. Mean intensity was measured from identical regions with in each image. Images, shown below, show a clear dose response for compound 124 in labeling cells. The bar graph shows the mean intensity of each image and supports the conclusions from visual inspection of the images. While BSA was used as a supplement, acylated BSA may be more practical.

The results of this experiment are provided below:

|  | 10 µM | 25 µM | 50 µM |
|---|---|---|---|
| Mean | 312.8 | 360.4 | 545.5 |
| Standard error | 2.3 | 9.3 | 1.6 |

These results demonstrate a dose dependent response.

Correlation between Folic Acid Receptors and Fluorescence Intensity

In this experiment, the procedures set forth above were repeated with the exception that SKOV3 cells were replaced with MCF7 cells—a breast cancer cell line that expresses folate binding protein albeit at a level lower than that of the SKOV3 cells. Upon completion of the experiment, the MCF7 cells also exhibited fluorescence upon exposure to UV light indicating binding and absorption of the conjugate coupled with conversion of the profluorescent moiety to the fluorescent moiety. However, the fluorescent intensity generated by the MCF7 cells was less than that generated by SKOV3 cells. Taken together, this data demonstrates that under identical conditions the number of folate binding proteins (folic acid receptors, e.g, FRα) on a cell correlates well with the amount of fluorescence generated by application of the conjugates of this invention to said cells.

Specifically, MCF cells were labeled at 10 uM with compound 24 for one hour in folate-free RPMI, no FBS. Cells were washed and imaged. Generally labeling is faint with the exception of the large round cells, which are dead.

It is well established that the expression of FRα in normal tissues is restricted to the luminal surface of the kidney, intestine, lung, retina, placenta and choroid plexus. Moreover, all of these normal tissues except the kidneys, the receptor is confined to the apical surface of the epithelium that is out of direct contact with folate and any folate receptor-targeting agents in the circulation. In normal kidney cells, folate is not retained by the kidney and, as such, is not relevant. Cheung, et al., Oncotarget, Vol. 7, No. 32, pp. 52553-52574 (2016).

Evaluation of Differential Fluorescence Imaging

The following example assesses the feasibility of detecting varying levels of fluorescence from minute to intense by differential analysis of the color green in a high definition digital picture. Fluorescence from fluorescein-based compounds is characteristically green when illuminated with UV light.

Specifically, the first image as found in FIG. 1 was of fluorescence generated from agar mixed with fluorescein. The gelatinous agar was then crumbled into various sizes from minute to relatively large particles to represent different fluorescent cancer cell masses of varying sizes and shapes in a surgical field. The first image consists of pixels that comprise red, green and blue values. A pixel-by-pixel analysis was conducted of the entire image to separate those where the green component had a value greater than background. The target pixels were arbitrarily assigned a red color to rapidly evaluate the differential fluorescence. The color so assigned is typically that which contrasts most effectively against background.

The pixel-by-pixel analysis allows for simultaneous selection of both very low fluorescence and exceptionally high fluorescence. In such a discriminatory analysis, the software can be used to selectively assign a marking color, other than green, to the green pixels which are less than a certain brightness, representative of normal cells. At the same time, other green pixels that exceed a certain brightness can be assigned a marking color, other than green, that will be representative of dead cells. In so doing, this process will remove extraneous cell data and allow the clinician to visualize only those viable cells that are likely cancerous.

The results of this analysis are set forth in FIG. 2. Those pixels that showed green values above background levels were construed to be representative of fluorescence generated by the fluorescein. In this image, there are numerous flagged pixels that are otherwise not visible or are difficult to visualize in FIG. 1. These results demonstrate that differential fluorescence analysis does detect minute levels of fluorescence both in real-time and in an interactive manner. The resulting image provides for otherwise non-detectible or difficult to detect cancer cell masses that heretofore likely escaped detection.

The invention claimed is:

1. A method for identifying cancer cells overexpressing folic acid receptors in a cell population suspected of containing cancer cells, normal cells and dead cells, said method comprising:
   a) applying an effective amount of a composition comprising a conjugate to said cell population wherein said conjugate comprises a folic acid or pteroic acid targeting moiety covalently coupled to a pro-fluorescent fluorescein based moiety optionally through a linker wherein said conjugate is selected from:

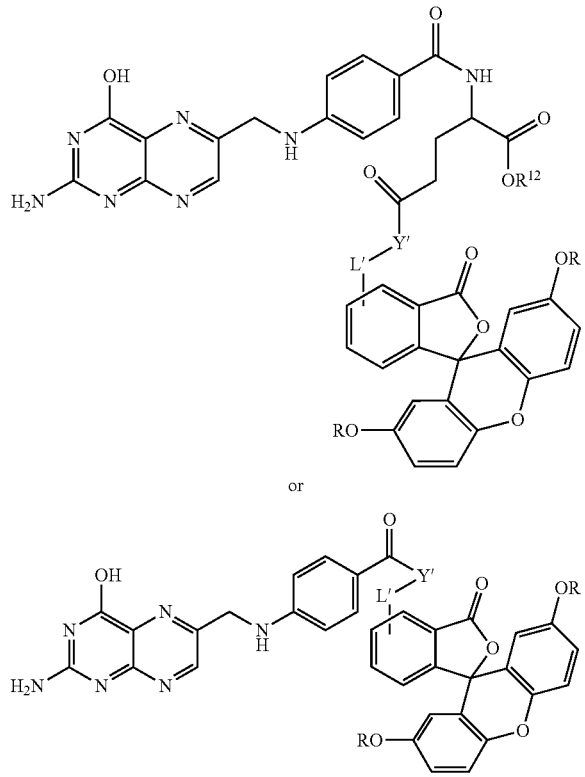

where each R is independently selected from —C(O)R$^1$ and —C(O)NHR$^1$ where R$^1$ is alkyl or substituted alkyl of from 4 to 30 carbon atoms;

R$^{12}$ is hydrogen or C$_1$-C$_6$ alkyl;

L' is a bond or a linker having from 1 to 20 atoms selected from the group consisting of oxygen, carbon, carbonyl, nitrogen, sulfur, sulfinyl, and sulfonyl;

Y' is oxygen, or NHR$^{11}$ where R$^{11}$ is hydrogen, C$_1$-C$_6$ alkyl, substituted C$_1$-C$_6$ alkyl, phenyl, substituted phenyl, cycloalkyl, substituted phenyl, cycloalkyl, substituted cycloalkyl, heteroaryl, substituted heteroaryl, heterocyclic, substituted heterocyclic; and or salts, tautomers and/or solvates thereof, b) incubating said composition with said cells for a sufficient period of time to permit said conjugate to bind to folic acid receptors on said cells coupled with intracellular conversion of said pro-fluorescent moieties to fluorescent moieties;

c) initiating fluorescence within said cell population due to fluorescein;

d) evaluating the intensity of fluorescein fluorescence on a pixel-by-pixel basis;

e) discriminating said pixels having less than a first predetermined threshold as background or non-cancerous in nature;

f) discriminating said pixels having more than a second predetermined threshold as arising from dead cells;

g) altering said discriminated pixels in e) and f) to marker pixels;

h) generating an altered image consisting of pixels associated with fluorescein fluorescence that have not been discriminated against; and i) assigning said non-discriminated pixels to cancer cells.

2. The method according to claim 1, wherein the pixels associated with cancer cells comprise green pixels.

3. The method according to claim 1, wherein the pixels associated with cancer cells are displayed on a screen in a surgical environment.

* * * * *